(12) United States Patent
Gilbert et al.

(10) Patent No.: US 7,354,897 B2
(45) Date of Patent: Apr. 8, 2008

(54) METHOD AND COMPOSITION FOR INHIBITING OR SLOWING BLOOD COAGULATION

(75) Inventors: Gary E. Gilbert, Winchester, MA (US); Jialin Shi, Newton, MA (US)

(73) Assignees: Brigham & Women's Hospital, Inc., Boston, MA (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 10/516,450

(22) PCT Filed: Jun. 6, 2003

(86) PCT No.: PCT/US03/15404

§ 371 (c)(1),
(2), (4) Date: Dec. 2, 2004

(87) PCT Pub. No.: WO03/103700

PCT Pub. Date: Dec. 18, 2003

(65) Prior Publication Data

US 2006/0035816 A1    Feb. 16, 2006

Related U.S. Application Data

(60) Provisional application No. 60/386,562, filed on Jun. 7, 2002.

(51) Int. Cl.
*A61K 38/00* (2006.01)
(52) U.S. Cl. .................................................... 514/2
(58) Field of Classification Search .............. None
See application file for complete search history.

(56) References Cited

U.S. PATENT DOCUMENTS

| | | |
|---|---|---|
| 4,725,442 A | 2/1988 | Haynes |
| 5,120,537 A | 6/1992 | Esmon et al. |
| 5,258,497 A | 11/1993 | Reutelingsperger et al. |
| 5,344,758 A | 9/1994 | Krilis et al. |
| 5,455,031 A | 10/1995 | Ceriani et al. |
| 5,505,955 A | 4/1996 | Peterson et al. |
| 5,632,986 A | 5/1997 | Tait et al. |
| 5,667,797 A | 9/1997 | Peterson et al. |
| 5,783,662 A | 7/1998 | Janmey et al. |
| 5,846,743 A | 12/1998 | Janmey et al. |
| 5,849,600 A | 12/1998 | Nixon et al. |
| 5,874,409 A | 2/1999 | Victoria et al. |
| 5,955,437 A | 9/1999 | Reutelingsperger |
| 5,972,337 A | 10/1999 | Ceriani et al. |
| 6,194,214 B1 | 2/2001 | Kraus |
| 6,284,475 B1 | 9/2001 | Rand |
| 6,312,694 B1 | 11/2001 | Thorpe et al. |
| 6,410,775 B1 | 6/2002 | Victoria et al. |
| 2003/0022221 A1 | 1/2003 | Langit et al. |
| 2004/0197314 A1 | 10/2004 | Delcayre et al. |
| 2004/0241179 A1 | 12/2004 | Raposo et al. |

FOREIGN PATENT DOCUMENTS

| | | |
|---|---|---|
| EP | 1004664 A1 | 5/2000 |
| WO | WO 00/30667 | 6/2000 |
| WO | WO2005/005954 A2 | 1/2005 |

OTHER PUBLICATIONS

Aoki et al., "Stage specific expression of milk fat globule membrane glycoproteins in mouse mammary gland: comparison of MFG-E8, butyrophilin, and CD36 with a major milk protein, beta casein", Biochimica et Biophysica Acta 1334: 182-190 (1997).*
Shi et al., "Lactadherin binds selectively to membrane containing phosphatidyl-L-serine and increased curvature", Biochimica et Biophysica Acta 1667: 82-90 (2004).*
Ortel et al. *Deletion analysis of recombinant human factor V. Evidence for a phosphatidylserine binding site in the second C-type domain.* J. Biol. Chem. Feb. 25, 1992, vol. 267, No. 6, pp. 4189-4198.
Larocca et al. *A Mr 46,000 human milk fat globule protein that is highly expressed in human breast tumors contains factor VIII-like domains.* Cancer Res. Sep. 15, 1991, vol. 51, No. 18, pp. 4994-4998.
Ortel et al. *Characterization of an acquired inhibitor to coagulation factor V. Antibody binding to the second C-type domain of factor V inhibits the binding of factor V to phosphatidylserine and neutralizes procoagulant activity.* J. Clin. Invest. Dec. 1992, vol. 90, pp. 2340-2347.
Hvarregaard J, Andersen MH, Berglund L, Rasmussen JT, Petersen TE. Characterization of glycoprotein PAS-6/7 from membranes of bovine milk fat globules. Eur J Biochem. 1996;240:628-636.
Stubbs J, Lekutis C, Singer K, et al. cDNA cloning of a mouse mammary epithelial cell surface protein reveals the existence of epidemal growth factor-like domains linked to factor VIII-like sequences. Proc Natl Acad Sci, USA. 1990;87:8417-8421.
Couto JR, Taylor MR, Godwin SG, Ceriani RL, Peterson JA. Cloning and sequence analysis of human breast epithelial antigen BA46 reveals an RGD cell adhesion sequence presented on an epidermal growth factor-like domain. DNA Cell Biol. 1996;15:281-286.
Andersen MH, Berglund L, Rasmussen JT, Petersen TE. Bovine PAS-6/7 binds $a_vb_5$ integrin and anionic phospholipids through two domains. Biochem. 1997;36:5441-5446.
Taylor MR, Couto JR, Scallan CD, Ceriani RL, Peterson JA. Lactadherin (formerly BA46), a membrane-associated glycoprotein expressed in human milk and breast carcinomas, promotes Arg-Gly-Asp (RGD)-dependent cell adhesion. DNA Cell Biol. 1997;16:861-869.
Andersen MH, Graversen H, Fedosov SN, Petersen TE, Rasmussen JT. Functional analyses of two cellular binding domains of bovine lactadherin. Biochem. 2000;39:6200-6206.

(Continued)

*Primary Examiner*—Robert Mondesi
*Assistant Examiner*—Anand Desai
(74) *Attorney, Agent, or Firm*—Dinesh Agarwal, P.C.

(57) ABSTRACT

A method and composition for inhibiting or slowing blood coagulation includes lactadherin, a fragment of lactadherin, a functional equivalent of lactadherin, or a functional equivalent of a fragment of lactadherin.

6 Claims, 7 Drawing Sheets

OTHER PUBLICATIONS

Butler JE, Pringnitz DJ, Martens CL,Crouch N. Bovine-associated mucoprotein: I. Distribution among adult and fetal bovine tissues and body fluids. Differentiation. 1980;17:31-40.
Newburg DS, Peterson JA, Ruiz-Palacios GM, et al. Role of human-milk lactadherin in protection against symptomatic rotavirus infection. Lancet. 1998;351:1160-1164.
Peterson JA, Couto JR, Taylor MR,Ceriani RL. Selection of tumor-specific epitopes on target antigens for radioimmunotherapy of breast cancer. Cancer Res. 1995;55:5847s-5851s.
Haggqvist B, Naslund J, Sletten K, et al. Medin: an integral fragment of aortic smooth muscle cell-produced lactadherin forms the most common human amyloid. Proc Natl Acad U S A. 1999;96:8669-8674.
Ensslin M, Calvete JJ, Thole HH, et al. Identification by affinity chromatography of boar sperm membrane- associated proteins bound to immobilized porcine zona pellucida. Mapping of the phosphorylethanolamine-binding region of spermadhesin AWN. Biol Chem Hoppe Seyler. 1995;376:733-738.
Arai M, Scandella D,Hoyer L. Molecular basis of factor VIII inhibition by human antibodies. Antibodies that bind to the factor VIII light chain prevent the interaction of factor VIII with phospholipid. J Clin Invest. 1989;83:1978-1984.
Foster PA, Fulcher CA, Houghten RA,Zimmerman TS. Synthetic factor VIII peptides with amino acid sequences contained within the C2 domain of factor VIII inhibit factor VIII binding to phosphatidylserine. Blood. 1990;75:1999-2004.
Ortel T, Devore-Carter D, Quinn-Allen M,Kane W. Deletion analysis of recombinant human factor V: Evidence for a phosphatidylserine binding site in the second C-type domain. J Biol Chem. 1992;267:4189-4198.
Gilbert GE, Furie BC,Furie B. Binding of human factor VIII to phospholipid vesicles. J Biol Chem. 1990;265:815-822.
Gilbert GE, Drinkwater D, Barter S,Clouse SB. Specificity of phosphatidylserine-containing membrane binding sites for factor VIII: Studies with model membranes supported by glass microspheres (Lipospheres). J Biol Chem. 1992;267:15861-15868.
Gilbert GE,Drinkwater D. Specific membrane binding of factor VIII is mediated by O-phospho-L-serine, a moiety of phosphatidylserine. Biochem. 1993;32:9577-9585.
Comfurius P, Smeets EF, Willems GM, Bevers EM,Zwaal RFA. Assembly of the prothrombinase complex on lipid vesicles depends on the stereochemical configuration of the polar headgroup of phosphatidylserine. Biochem. 1994;33:10319-10324.
Gilbert GE,Arena AA. Phosphatidylethanolamine induces high affinity binding sites for factor VIII on membranes containing phosphatidyl-L-serine. J Biol Chem. 1995;270:18500-18505.
Gilbert GE,Arena AA. Unsaturated phospholipid acyl chains are required to constitute membrane binding sites for factor VIII. Biochem. 1998;37:13526-13535.
Pratt KP, Shen BW, Takeshima K, et al. Structure of the C2 domain of human factor VIII at 1.5 angstrom resolution. Nature. 1999;402:439-442.
Macedo-Ribeiro S, Bode W, Huber R, et al. Crystal structures of the membrane-binding C2 domain of human coagulation factor V. Nature. 1999;402:434-439.
Kim SW, Quinn-Allen, MA, Camp JT, et al. Identification of functionally important amino acid residues within the C2-domain of human factor V using alanine-scanning mutagenesis. Biochem. 2000;39:1951-1958.
Peterson JA, Patton S,Hamosh M. Glycoproteins of the human milk fat globule in the protection of the breast-fed infant against infections. Biol Neonate. 1998;74:143-162.
Tait JF, Gibson D,Fujikawa K. Phospholipid binding properties of human placental anticoagulent protein-1, a member of the lipocortin family. J Biol Chem. 1989;264:7944-7949.
Crompton MR, Moss SE,Crumpton MJ. Diversity in the lipocortin/calpactin family. Cell. 1988;55:1-3.
Swairjo MA, Concha NO, Kaetzel MA, Dedman JR,Seaton BA. Ca2+-bridging mechanism and phospholipid head group recognition in the membrane-binding protein annexin V. Nat Struct Biol. 1995;2:968-974.

Tait JF, Sakata MS, McMullen BA, et al. Placental anticoagulent proteins: Isolation and comparative characterization of four members of the lipocortin family. Biochem. 1988;27:6268-6276.
Gilbert GE,Arena AA. Activation of the factor VIIIa-factor IXa enzyme complex of blood coagulation by membranes containing phosphatidyl-L-serine. J Biol Chem. 1996;271-11120-11125.
Bangham AD, Standish MM,Watkins JC. Diffusion of univalent ions across the lamellae of swollen phospholipids. J Mol Biol. 1965;13:238-252.
Johnson SM, Bangham AD, Hill MW,Korn ED. Single bilayer liposomes. Biochim Biophys Acta. 1971;233:820-826
Hope MJ, Bally MB, Webb G,Cullis PR. Production of large unilamellar vesicles by a rapid extrusion procedure. Characterization of size distribution, trapped volume and ability to maintain a membrane potential. Biochim Biophys Acta. 1985;812:55-65.
Chen P, Toribara T,Warner H. Anal Chem. 1956;28:1756-1758.
Neuenschwander PF,Morrissey JH. Deletion of the membrane anchoring region of tissue factor abolishes autoactivation of factor VII but not cofactor function. Analysis of a mutant with a selective deficiency in activity. J Biol Chem. 1992;267:14477-14482.
Lollar P,Fass DN. Inhibition of activated porcine factor IX by dansyl-glutamyl-glycyl-arginyl-chloromethylketine. Arch Biochem Biophys. 1984;233:438-446.
Gilbert GE, Sims PJ, Wiedmer T, et al. Platelet-derived microparticles express high affinity receptors for factor VIII. J Biol Chem. 1991,266:17261-17268.
Govers-Riemslag JW, Janssen MP, Zwaal RF,Rosing J. Prothrombin activation on dioleoylphosphatidylcholine membranes. Eur J Biochem. 1994;220:131-138.
Andree HA, Stuart MC, Hermens WT, et al. Clustering of lipid-bound annexin V may explain its anticoagulant effect. J Biol Chem. 1992;267:17907-17912.
Huang C,Mason J. Geometric packing constraints in egg phosphatidylcholine vesicles. Proc Natl Acad Sci, USA. 1978;75:308-310.
Andreee H, Reutelingsperger C, Hauptmann R, et al. Binding of vascular anticoagulant a (VACa) to planar phospholipid bilayers. J Biol Chem. 1990;265:4923-4928.
Ueno M, Tanford C,Reynolds JA. Phospholipid vesicle formation using nonionic detergents with low monomer solubility. Kinetic factors determine vesicle size and permeability. Biochem. 1984;23:3070-3076.
Mann KG, Nesheim ME, Church WR, Haley P,Krishnaswamy S. Surface-dependent reactions of the vitamin K-dependent enzyme complexes. Blood. 1990;76:1-16.
Freyssinet JM, Gauchy J,Cazenave JP. The effect of phospholipids on the activation of protein C by the human thrombin-thrombomodulin complex. Biochem J. 1986;238:151-157.
Suzuki K, Stenflo J, Dahlback B,Teodorsson B. Inactivation of human coagulation factor V by activated protein C. J Biol Chem. 1983;258:1914-1920.
Connor J,Schroit A. Transbilayer movement of phosphatidylserine in erythrocytes: Inhibition of transport and preferential labeling of a 31000-dalton protein by sulfhydryl reactive reagents. Biochem. 1988;27:848-851.
Connor J, Bucana C, Fidler IJ,Schroit AJ. Differentiation-dependent expression of phosphatidylserine in mammalian plasma membranes: Quantitative assessment of outer-leaflet lipid by prothrombinase complex formation. Proc Natl Acad Sci USA. 1989;86:3184-3188.
Fadok VA, Voelker DR, Campbell PA, et al. Exposure of phosphatidylserine on the surface of apoptotic lymphocytes triggers specific recognition and removal by macrophages. J Immunol. 1992;148:2207-2216.
Bevers E, Comfurius P,Zwaal R. Changes in membrane phospholipid distribution during platelet activation: Biochim Biophys Acta. 1983;736:57-66.
van Heerde WL, Poort S, van 't Veer C, Reutelingsperger CP, de Groot PG. Binding of recombinant annexin V to endothelial cells: effect of annexin V binding on endothelial-cell-mediated thrombin formation. Biochem J. 1994;302 ( Pt 1):305-312.

London F, Ahmad SS,Walsh PN. Annexin V inhibition of factor IXa-catalyzed factor X activation on human platelets and on negatively-charged phospholipid vesicles. Biochem. 1996;35:16886-16897.

Nimpf J, Bevers EM, Bomans PH, et al. Prothrombinase activity of human platelets is inhibited by beta 2-glycoprotein-I. Biochim Biophys Acta. 1986;884:142-149.

Mori T, Takeya H, Nishioka J, Gabazza EC, Suzuki K. beta 2-Glycoprotein I modulates the anticoagulant activity of activated protein C on the phospholipid surface. Thromb Haemost. 1996;75:49-55.

McNeil HP, Simpson RJ, Chesterman CN,Krilis SA. Antiphospholipid antibodies are directed against a complex antigen that includes a lipid-binding inhibitor of coagulation: beta 2-glycoprotein I (apolipoprotein H). Proc Natl Acad Sci U S A. 1990;87:4120-4124.

Takeya H, Mori T, Gabazza EC, et al. Anti-beta2-glycoprotein I (beta2GPI) monoclonal antibodies with lupus anticoagulant-like activity enhance the beta2GPI binding to phospholipids. J Clin Invest. 1997;99:2260-2268.

Bancsi LF, van der Linden IK,Bertina RM. Beta 2-glycoprotein I deficiency and the risk of thrombosis. Thromb Haemost. 1992;67:649-653.

Ceriani RL, Sasaki M, Sussman H, Wara WM,Blank EW. Circulating human mammary epithelial antigens in breast cancer. Proc Natl Acad Sci U S A. 1982;79:5420-5424.

Enoch HG, Strittmatter P. Formation of properties of 1000-Å-diameter, single-bilayer phospholipid vesicles. Proceeding of the National Academy of Scienes, USA 1979;76:145-149.

Hanayama R, Tanaka M, Miwa K, Shinohara A, Iwamatsu A, Nagata S. Identification of a factor that links apoptotic cells to phagocytes. Nature 2002;417(6885):182-7.

Shi J, Gilbert GE. Lactadherin inhibits enzyme complexes of blood coagulation by competing for phospholipid binding sites. Blood 2003;101(7):2628-36.

Bardelle C, Furie B, Furie BC, Gilbert GE. Kinetic Studies of Factor VIII Binding to Phospholipid Membranes Indicate a Complex Binding Process. J. Biol. Chem. 1993;268:8815-24.

Gilbert GE, Kaufman RJ, Arena AA, Miao H, Pipe SW. Four hydrophobic amino acids of the factor VIII C2 domain are constituents of both the membrane-binding and von Willebrand factor-binding motifs. J Biol Chem 2002;277(8):6374-81.

Dachary-Prigent J, Freyssinet JM, Pasquet JM, Carron JC, Nurden AT. Annexin V as a probe of aminophospholipid exposure and platelet membrane vesiculation: a flow cytometry study showing a role for free sulfhydryl groups. Blood 1993;81(10):2554-65.

Alberio L, Safa O, Clemetson KJ, Esmon CT, Dale GL. Surface expression and functional characterization of alpha-granule factor V in human platelets: effects of ionophore A23187, thrombin, collagen, and convulxin. Blood 2000;95(5):1694-702.

Zwaal R, Comfurius P, van Deenen L. Membrane asymmetry and blood coagulation. Nature 1977;268:358-360.

Bevers E, Comfurius P, Van Rijn J, Hemker H, Zwaal R. Generation of Prothrombin-Coverting Activity and the Exposure of Phosphatidylserine at the Outer Surface of Platelets. Eur. J. Biochem. 1982;122:429-436.

Seigneuret M, Devaux PF. ATP-dependent asymmetric distribution of spin-labeled phospholipids in the erythrocyte membrane: Relation to shape changes. Proc. Natl. Acad. Sci., USA 1984;81:3751-3755.

Tracy P, Peterson J, Neshiem M, McDuffie F, Mann K. Interaction of coagulation factor V and factor Va with platelets. J. Biol. Chem. 1979;254:10345.

Swords NA, Tracy PB, Mann KG. Intact Platelet Membranes, Not Platelet-Released Microvesicles, Support the Procoagulant Activity of Adherent Platelets. Arterioscler. Thromb. 1993;13(11):1613-1622.

Ahmad SS, Rawala-Sheikh R, Ashby B, Walsh PN. Platelet receptor-mediated factor X activation by factor IXa: High-affinity factor IXa receptors induced by factor VIII are deficient on platelets in Scott syndrome. J. Clin. Invest. 1989;84:824-828.

Comfurius P, Bevers EM, Zwaal RFA. Enzymatic synthesis of phosphatidylserine on small scale by use of one-phase system. J. Lipid Res. 1990;31:1719-1721.

Pusey M, Mayer L, Wei G, Bloomfield V, Nelsestuen G. Kinetic and Hydrodynamic Analysis of Blood Clotting Factor V-Membrane Binding. Biochemistry 1982;21:5262-5269.

Abbott A, Nelsestuen G. Association of a Protein with Membrane Vesicles at the Collisional Limit: Studies with Blood Coagulation Factor Va Light Chain Also Suggest Major Differences between Small and Large Unilamellar Vesicles. Biochemistry 1987;26:7994-8003.

Bloom JW. The interaction of rDNA factor VIII, factor VIIIdes-797-1562 and factor VIIdes-797-1562 derived peptides with phospholipid. Throm. Res. 1987;48:439-448.

Epand RM, Stevenson C, Bruins R, Schram V, Glaser M. The chirality of phosphatidylserine and the activation of protein kinase C. Biochemistry 1998;37(35):12068-73.

Berden JA, Barker RW, Radda GK. NMR studies on phospholipid bilayers. Some factors affecting lipid distribution. Biochem. Biophys. Acta 1975;375(2):186-208.

Barsukov LI, Victorov AV, Vasilenko IA, Evstigneeva RP, Bergelson LD. Investigation of the inside-outside distribution, intermembrane exhange and transbilayer movement of phospholipids in sonicated vesicles by shift reagent NMR. Biochim. Biophys. Acta 1980;598(1):153-68.

Litman BJ. Determination of molecular asymmetry in the phosphatidylethanolamine surface distribution in mixed phospholipid vesicles. Biochemistry 1974;13(14):2844-8.

Koynova RD, Tenchov BG. Effect of ion concentration on phosphatidylethanolamine distribution in mixed vesicles. Biochim. Biophys. Acta 1983;727(2):351-6.

Lentz BR, Litman BJ. Effect of head group on phospholipid mixing in small, unilamellar vesicles: mixtures of dimyristoylphosphatidylcholine and dimyristoylphosphatidylethanolamine. Biochemistry 1978;17(25):5537-43.

Nordlund JR, Schmidt CF, Dicken SN, Thompson TE. Transbilayer distribution of phosphatidylethanolamine in large and small unilamellar vesicles. Biochemistry 1981;20(11):3237-41.

Tait JF, Gibson D. Phospholipid binding of annexin V: effects of calcium and membrane phosphatidylserine content. Arch. Biochem. Biophys. 1992;298(1):187-91.

Pigault C, Follenius-Wund A, Schmutz M, Freyssinet JM, Brisson A. Formation of two-dimensional arrays of annexin V on phosphatidylserine-containing liposomes. J. Mol. Biol. 1994;236(1):199-208.

Koopman G, Reutelingsperger CP, Kuijten GA, Keehan RM, Pals ST, van Oers MH. Annexin V for flow cytometric detection of phosphatidylserine expression on B cells undergoing apoptosis. Blood 1994;84(5):1415-20.

Connor J, Bucana C, Fidler IJ, Schroit AJ. Differentiation-dependent expression of phosphatidylserine in mammalian plasma membranes: Quantitative assessment of outer-leaflet lipid by prothrombinase complex formation. Proc. Natl. Acad. Sci. USA 1989;86:3184-3188.

Poste G, Papahadjopoulos D. Lipid vesicles as carriers for introducing materials into cultured cells: influence of vesicle lipid composition on mechanism(s) of vesicle incorporation into cells. Proc. Natl. Acad. Sci. U. S. A. 1976;73(5):1603-7.

Batzri S, Korn ED. Interaction of phospholipid vesicles with cells. Endocytosis and fusion as alternate mechanisms for the uptake of lipid-soluble and water-soluble molecules. J. Cell Biol. 1975;66(3):621-34.

Chang CP, Zhao J, Wiedmer T, Sims PJ. Contribution of platelet microparticle formation and granule secretion to the transbilayer migration of phosphatidylserine. J. Biol. Chem. 1993;268:7171-7178.

McIntyre JC, Sleight RG. Fluorescence Assay for Phospholipid Membrane Assymetry. Biochemistry 1991;30:11819-11827.

Lawler J, Hynes RO. An integrin receptor on normal and thrombasthenic platelets that binds thrombospondin. Blood 1989;74(6):2022-7.

Bevers E, Wiedmer T, Comfurius P, Shattil S, Weiss H, Zwaal R, et al. Defective Ca2+-Induced Microvesiculation and Deficient Expression of Procoagulant Activity in Erythrocytes From a Patient With a Bleeding Disorder: A Study of the Red Blood Cells of Scott Syndrome. Blood 1992;79:380-388.

Jain MK, Rogers J, Marecek JF, Ramirez F, Eibl H. Effect of the Structure of phospholipid on the kinetics of intravesicle scooting of phospholipase A2. Biochim. Biophys. Acta 1986;860(3):462-74.

Kim DH, Azuma N, Tanaka H, Kanno C. Structures of the N-linked sugar chains in the PAS-6 glycoprotein from the bovine milk fat globule membrane. Glycoconjugate Journal 1998; 15:361-369.

Shi J, Gilbert GE. Lactadherin inhibits enzyme complexes of blood coagulation by competing for phospholipid binding sites. Blood Dec. 2002;100(11):262a, American Society of Hematology Abstract (1 page).

* cited by examiner

METHOD AND COMPOSITION FOR INHIBITING OR SLOWING BLOOD COAGULATION

CROSS-REFERENCE TO RELATED APPLICATIONS

The present application claims priority on prior U.S. Provisional Application Ser. No. 60/386,562, filed Jun. 7, 2002, and which is incorporated herein in its entirety by reference.

STATEMENT REGARDING FEDERALLY SPONSORED RESEARCH OR DEVELOPMENT

The work leading to the present invention was supported by one or more grants from the U.S. Government, including National Heart, Lung, and Blood Institute Grant R01 HL57867. The U.S. Government therefore has certain rights in the invention.

BACKGROUND OF THE INVENTION

The present invention is generally directed to inhibiting or slowing blood coagulation, and more particularly to using lactadherin or a fragment thereof as an agent for inhibiting or slowing blood coagulation.

There are several anticoagulant drugs which are in widespread clinical use and many others in development, including clinical trials. However, none of these agents have the mechanism of blocking access of blood proteins to procoagulant membrane surfaces. Inhibition of coagulation at this stage is an earlier step than most anti-coagulants target and, it is specifically an anticoagulant step as opposed to a step which would inhibit platelet aggregation or adhesion.

Investigators have sought anticoagulants that would work via this mechanism for decades. Phospholipases from snake venoms can function as anticoagulants by competing for membrane binding sites and the function of several phospholipases have been analyzed in detail. These proteins are unsuitable for use in humans because the corresponding enzymatic activity (phospholipases cleave phospholipids releasing lysophospholipids and free fatty acids) cause inflammation and tissue injury. A single class of agents, annexins, have been shown to inhibit blood coagulation by blocking the membrane surface. These proteins have been evaluated as anticoagulants in animals. The efficacy is modest, at least partly because annexin is more fastidious in its requirements for membrane lipids than most blood clotting proteins. Thus, much of the procoagulant membrane of cells remains unblocked, even with a vast excess of annexin V. We compared the anticoagulant efficacy of annexin V directly to that of lactadherin.

Lactadherin is a MW 47,000 glycoprotein of milk fat globules. It has also been known as PAS-6/7, indicating the two glycosylation variants (Reference 1), bovine-associated mucoprotein, BA-46, P47, and MFG-E8 (Reference 2). Lactadherin has a domain structure of EGF1-EGF2-C1-C2 in which EGF indicates epidermal growth factor homology domains, and the C domains share homology with the discoidin family including the lipid-binding "C" domains of blood coagulation factor VIII and factor V (FIG. 1) (Reference 2). The second EGF domain displays an Arg-Gly-Asp motif (Reference 3) which binds to the $\alpha_v\beta_5$ and $\alpha_v\beta_5$ integrins (References 1 and 4-6). The second C domain binds to phospholipids (Reference 6).

In milk fat globules, lactadherin lines the surface of the phospholipid bilayer which surrounds the central triglyceride droplet, apparently stabilizing the bilayer (Reference 7). Lactadherin decreases the symptoms of rotavirus infection in infants, possibly by binding to rotavirus particles via carbohydrate moieties (Reference 8). In tissue sections, lactadherin is found localized on the apical portion of secretory epithelium in the breast (Reference 7). Abundant expression by breast carcinoma tissue makes lactadherin a potential target for antigen-guided radiation therapy (Reference 9). Lactadherin is also found on the apical surface of epithelia in the biliary tree, the pancreas, and sweat glands (Reference 7) and is synthesized by aortic medial smooth muscle cells (Reference 10). Function in these tissues remains unknown. Lactadherin has been identified as a zona pellucida-binding protein on the acrosomal cap of sperm (Reference 11).

Blood coagulation factor VIII and factor V bind to phospholipid membranes via "C" domains which share homology with lactadherin (References 12-14). Remarkable features of membrane binding for these proteins include high affinity ($K_D$ approx. 2 nM) (Reference 15) and sufficient specificity so that no plasma proteins compete for membrane binding sites (Reference 16). Factor VIII binds via stereoselective interaction with the phospho-$_L$-serine motif of phosphatidylserine (PS) (Reference 17). Factor V also exhibits stereoselective interaction with PS (Reference 18). Binding of factor VIII is enhanced by the presence of phosphatidylethanolamine (PE) in the membrane (Reference 19), by unsaturated phospholipid acyl chains (Reference 20), and by membrane curvature (Reference 19). The crystal structures of the C2 domains of factors VIII and V suggest that membrane binding is mediated by two pairs of hydrophobic residues displayed at the tips of β-hairpin turns (References 21-22). Mutagenesis studies have confirmed the role of these residues in phospholipid binding (Reference 23). The homology of the lactadherin C domains with those of factors VIII and V suggests that similar phospholipid binding properties may exist. Indeed, lactadherin has been found to bind selectively to PS (Reference 24) and to utilize primarily the C2 domain in its lipid binding (Reference 6).

Annexin V, like factor VIII and factor V, exhibits high affinity, PS-dependent membrane binding (Reference 25). However, the quadruplicate membrane-binding motifs of annexin V are not homologous with the discoidin-like domains of lactadherin, factor VIII, and factor V (Reference 26). Corresponding to the difference in structure, the membrane binding mechanism is different. In addition, annexin V requires $Ca^{++}$ for membrane-binding and the binding is chiefly hydrophilic in nature (Reference 27). Annexin V does have the capacity to compete for a fraction of the phospholipid binding sites utilized by the factor VIIIa-factor IXa enzyme complex and the factor Xa-factor Va enzyme complex of the coagulation cascade so that it functions in vitro as a membrane-blocking anticoagulant (Reference 28). The well-defined membrane-binding and anti-coagulant properties of annexin V make studies with annexin V suitable controls for studies with lactadherin.

OBJECTS AND SUMMARY OF THE INVENTION

The principal object of the present invention is to provide an agent which inhibits or slows blood coagulation. The agent includes lactadherin, a fragment of lactadherin, a functional equivalent of lactadherin, or a functional equivalent of a fragment of lactadherin.

An object of the present invention is to provide an agent which inhibits or slows blood coagulation by competing for membrane binding sites of factor VII and/or factor V.

Another object of the present invention is to provide an agent which inhibits or slows blood coagulation by inhibiting the prothrombinase complex and the factor VII a-tissue factor complex.

Yet another object of the present invention is to provide an agent which inhibits or slows clotting of whole blood.

Still yet another object of the present invention is to provide an agent which inhibits or slows coagulation reactions on cell membranes.

An additional object of the present invention is to provide an agent which is an efficient inhibitor of the prothrombinase and the factor Xase complex regardless of the degree of membrane curvature and/or the phosphatidylserine content.

Yet an additional object of the present invention is to provide an agent which is more effective than annexin V in inhibiting or slowing blood coagulation or clotting.

Lactadherin, a glycoprotein of the milk fat globule membrane, contains tandem C-domains with homology to discoidin-type lectins and to membrane-binding domains of blood-clotting factors V and VIII. We investigated whether the structural homology confers the capacity to compete for the membrane-binding sites of factor VIII and factor V and to function as an anticoagulant. Our results indicate that lactadherin competes efficiently with factor VIII and factor V for binding sites on synthetic phosphatidylserine-containing membranes with half-maximal displacement at lactadherin concentrations of 1-4 nM. Binding competition correlated to functional inhibition of factor VIIIa-factor IXa (factor Xase) enzyme complex. In contrast to annexin V, lactadherin was an efficient inhibitor of the prothrombinase and the factor Xase complexes regardless of the degree of membrane curvature and the phosphatidylserine content. Lactadherin also inhibited the factor VIIa-tissue factor complex efficiently whereas annexin V was less effective. Since the inhibitory concentration of lactadherin was proportional to the phospholipid concentration, and because lactadherin was not an efficient inhibitor in the absence of phospholipid, the major inhibitor effect of lactadherin relates to blocking phospholipid sites rather than forming inhibitory protein-protein complexes. Lactadherin was also found to be an effective inhibitor of a modified whole blood prothrombin time assay in which clotting was initiated by dilute tissue factor; 60 nM lactadherin prolonged the prothrombin time 150% vs. 20% for 60 nM annexin V. These results indicate that lactadherin functions as a potent phospholipid-blocking anticoagulant.

At least one of the above-noted objects is met, in part, by the present invention, which in one aspect includes blocking or reducing access to a procoagulant molecule by a coagulation molecule by subjecting a procoagulant molecule to lactadherin, a fragment of lactadherin, a functional equivalent of lactadherin, or a functional equivalent of a fragment of lactadherin.

Another aspect of the invention includes blocking or reducing binding of a ligand to cell membrane binding site by subjecting a cell membrane binding site to lactadherin, a fragment of lactadherin, a functional equivalent of lactadherin, or a functional equivalent of a fragment of lactadherin.

Another aspect of the invention includes inhibiting or slowing blood coagulation by subjecting a predetermined amount of blood to an effective amount of lactadherin, a fragment of lactadherin, a functional equivalent of lactadherin, or a functional equivalent of a fragment of lactadherin.

Another aspect of the invention includes inhibiting or slowing blood clotting by administering to a subject in need thereof an effective amount of lactadherin, a fragment of lactadherin, a functional equivalent of lactadherin, or a functional equivalent of a fragment of lactadherin.

Another aspect of the invention includes preventing or reducing inflammation by administering to a subject in need thereof an effective amount of lactadherin, a fragment of lactadherin, a functional equivalent of lactadherin, or a functional equivalent of a fragment of lactadherin.

Another aspect of the invention includes inhibiting or slowing blood coagulation by administering to a subject in need thereof an effective amount of lactadherin, a fragment of lactadherin, a functional equivalent of lactadherin, or a functional equivalent of a fragment of lactadherin.

Another aspect of the invention is to provide an anticoagulant reagent which includes lactadherin, a fragment of lactadherin, a functional equivalent of lactadherin, or a functional equivalent of a fragment of lactadherin. A pharmaceutical composition may be prepared by utilizing the anticoagulant reagent with a pharmaceutically acceptable carrier or diluent.

Another aspect of the invention includes removing a phospholipid from a biological fluid by providing a biological fluid including, or suspect of including, a phospholipid, subjecting the biological fluid to a suitable amount of a binding agent (lactadherin, a fragment of lactadherin, a functional equivalent of lactadherin, or a functional equivalent of a fragment of lactadherin) allowing binding between the phospholipid and the binding agent, and removing the binding agent with the phospholipid bound thereto.

BRIEF DESCRIPTION OF THE DRAWINGS

The above and other objects, novel features and advantages of the present invention will become apparent from the following detailed description of the invention, as illustrated in the drawings, in which.

DETAILED DESCRIPTION OF THE INVENTION

Figure 1:
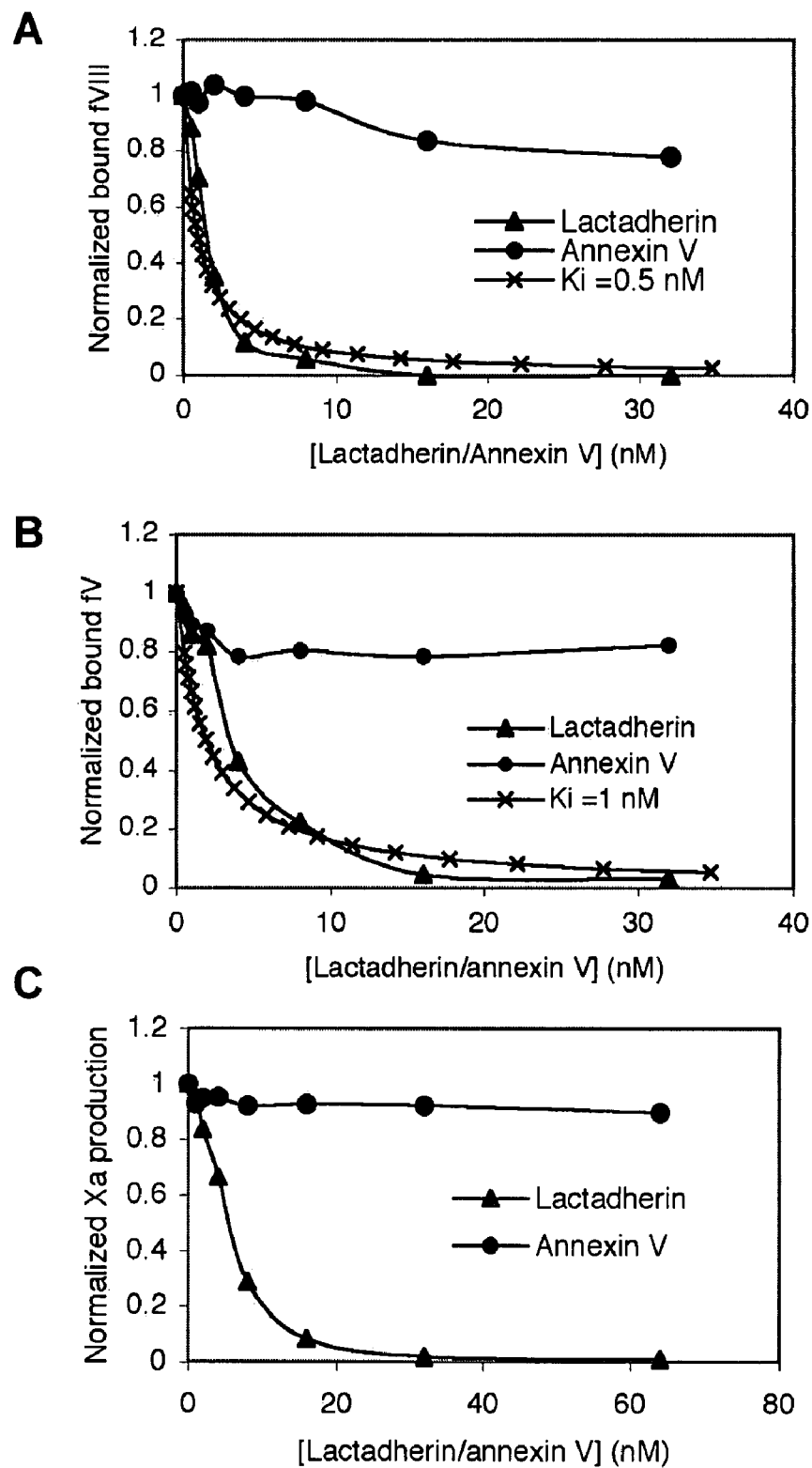
FIGS. 1A-C illustrate competition for factor VIII and factor V binding sites by lactadherin or annexin V.

The present invention is based, at least in part, on the discovery that lactadherin, a glycoprotein of milk fat globules, functions as an anticoagulant by competing with factors VIII and V for membrane binding sites. Our experiments below show that lactadherin functions as a potent phospholipid blocking anticoagulant.

Materials

Human factor X, human factor Xa, and human factor IXa were obtained from Enzyme Research Laboratories (South/Bend, Ind.), human factor V, human factor Va, and corn trypsin inhibitor were obtained from Heamatologic Technologies Inc. (Burlington, Vt.). Recombinant human factor VII was a gift from D. Pittman of Genetics Institute, Cambridge, Mass. Human factor VIIa, human prothrombin, and human α-thrombin were obtained from Enzyme Research Laboratories (South Bend, Ind.). Both recombinant human tissue-factor and lipidated recombinant human tissue-factor were obtained from American Diagnostca Inc. (Greenwich, Conn.). Lactadherin was a gift from Drs. C. W. Heegaard and J. T. Rasmussen of the Department of Molecular and Structural Biology, University of Aarhus, Denmark. Annexin V was obtined from Sigma. Bovine brain PS, egg yolk PE, and phosphatidylcholine (PC) were obtained from Avanti Polar Lipids (Alabaster, Ala.). Chromogenic substrate S-2238 and S-2765 were obtained from DiaPharma Group Inc (Westchester, Ohio).

Methods

Evaluation and Storage of Proteins

Pure bovine lactadherin was supplied at a concentration of 1 mg/ml in phosphate-buffered saline. SDS-PAGE with silver staining revealed only two bands corresponding to the previously described lactadherin doublet with approximate MWs of 47 kDa and 50 kDa. Lactadherin was stored at −80° C., aliquotted after thawing and each aliquot subjected to less than 3 cycles of flash-freezing and rapid thawing. The purity and handling of other proteins were as previously described (Reference 29).

Preparation of Phospholipid Vesicles

Phospholipid vesicles were prepared by evaporating chloroform from the desired phospholipids (PS %: PE %: PC %=4:20:76 and 15:20:65), resuspending in methylene chloride and re-evaporating twice under argon. Phospholipids were then suspended by gently swirling tris-buffered saline (50 mM Tris, 150 mM NaCl, pH 7.4) over the dried lipid suspension until all lipid was suspended. Vesicles prepared in this way were used as large multilamellar vesicles (LMV) (Reference 30). Some of the resuspended vesicles were then sonicated in a high intensity bath sonicator (Laboratory Supplies, Inc. Hicksville, N.Y.) (Reference 31) and some were made extruding these phospholipid suspensions twenty times through two stacked polycarbonate membranes (Millipore, Bedford, Mass.) in a High Pressure Extrusion Device (Sciema Technical Services, Vancouver, BC, Canada) under argon as described previously (Reference 32). Phospholipid concentration was determined by phosphorus assay (Reference 33). Vesicles were used fresh, or 1 ml aliquots were quick-frozen in liquid nitrogen, stored at −80° C., and thawed at 37° C. Storage at 4° C. before incubation with microspheres or blood clotting factors did not exceed 24 hours.

Relipidation of TF

Recombinant human tissue factor was relipidated into phospholipid vesicles of the indicated composition using the octyl-β-D-glucopyranoside method (Reference 34). The nominal molar ratios of TF to phospholipid monomer was 1:7500.

Fluorescein-Glu-Gly-Arg Chloromethyl Ketone Labeling of Factor IXa

Factor IXa was labeled with fluorescein-Glu-Gly-Arg chloromethyl ketone (Haematologic Technologies, Burlington, Vt.) essentially as described for the Dansyl-Glu-Gly-Arg chloromethyl ketone (Reference 35). Free fluorescein-peptide was removed by ultrafiltration (Centricon 30, Millipore Corp., Bedford, Mass.). Labeling efficiency, as judged by the ratio of absorbance at 280 nm to absorbance at 490 nm, divided by extinction coefficients for factor IXa and fluorescein, was 0.2 fluorescein-peptide:factor IXa.

Flow Cytometry Binding Assay

Lipospheres were prepared as previously described (Reference 16). Glass microspheres of 1.6 μm nominal diameter (Duke Scientific, Palo Alto, Calif.) were cleaned, size-restricted, incubated with sonicated vesicles of the indicated composition, washed three times in 0.15 M NaCl, 0.02 M Tris-HCl, 0.1% defatted bovine albumin, 10 μM egg PC as sonicated vesicles. Lipospheres were stored at 4° C. and used within 8 hours of synthesis. Recombinant human factor VIII and purified human factor V were labeled with fluorescein maleimide as described (Reference 36). Fluorescein-labeled factor VIII (4 nM) or fluorescein-labeled factor V (4 nM) were incubated with lactadherin or annexin V for 15 min at room temperature, the mixture was added to lipospheres for an additional 10 minutes, and membrane-bound fVIII or factor V was measured by flow cytometry. This procedure was performed on 25-μL aliquots of 100-μL samples with an approximate liposphere concentration of $1 \times 10^6$/mL using a Becton Dickinson FACSCalibur flow cytometer. Data acquisition was triggered by forward light scatter with all photomultipliers in the log mode. Noise was reduced during analysis by eliminating events with forward and side scatter values different from those characteristic of the lipospheres. Mean log fluorescence was converted to linear fluorescence for values depicted in the figures. Only experiments in which the fluorescence histogram indicated a log normal distribution, as judged by inspection, were analyzed quantitatively. Flow cytometry experiments were performed in 0.14 M NaCl, 0.02 M Trizma-HCl, 1.5 or 5 mM $CaCl_2$ as indicated in figure legends, and 0.1% bovine albumin, pH 7.5.

Mathematical Model

Competition of lactadherin for phospholipid binding sites of factor VIII was compared to the following model:

$$fVIIIB/fVIIIB(max) = [fVIII] / ((K_D*(1+[Lactadherin]/K_i)) + [fVIII])$$

where fVIIIB is membrane-bound factor VIII, fVIIIB (max) is maximum bound factor VIII when the concentration of factor VIII is saturating, $K_D$ is the dissociation constant of factor VIII with phospholipid binding sites, $K_i$ is the dissociation constant of lactadherin with the binding sites recognized by factor VIII. The model assumes that phospholipid binding sites are limiting. For the curves depicted in FIGS. 1-3, all data was normalized to the calculated value of fVIIIB/fVIIIB(max) at the indicated concentrations of factor VIII without lactadherin. For factor Xase complex activity fVIIIB/fvIIIB(max) was assumed to be proportional to residual activity. Curve fitting was by eye, while varying Ki, as the concentrations of factor VIII and lactadherin were known and the KD value for factor VIII (Reference 30) had been determined experimentally (see FIGS. 1A-C, where displayed results are from a single experiment representative of at least two experiments for all conditions). The same model, substituting fV for fVIII, was used for comparison to competition binding experiments with factor V and inhibition of the prothrombinase complex.

Factor Xase Assay

The activation of factor X by factor IXa in the presence of lactadherin or annexin V was measured with a two-step amidolytic substrate assay (Reference 29) with the following modifications. Factor IXa, 0.1 nM, was incubated with the specified concentrations of factor X and varied concentrations of lactadherin and annexin V in 150 mM NaCl, 50 mM Tris, pH 7.4, 1.5 mM $CaCl_2$ (for 4% PS, sonicated vesicle) or 5 mM $CaCl_2$ (for the other vesicles), 1 nM factor VIII, 0.1 nM thrombin for 5 min. at 25° C.; final reaction volume, 40 µl. The reaction was then stopped by the addition of EDTA to 7 mM final concentration. The amount of factor Xa generated was determined immediately using the chromogenic substrate S-2765 (0.31 mg/mL) on a Molecular Devices ELISA plate reader in kinetic mode. The results displayed in the figures are means of duplicates from a representative experiment. For studies without phospholipid, 40 nM factor IXa was mixed with 40 nM factor VIII and 250 nM factor X in the reaction buffer. The reaction was started by addition of 2 nM thrombin and 1.5 mM $Ca^{++}$. The reaction was allowed to proceed for 30 min. prior to quenching with EDTA and reading, as above.

Factor VIIa-Tissue Factor Assay

Relipidated tissue factor, at the indicated concentration, was mixed with factor X (100 nM), factor VIIa (100 pM) and varied concentrations of lactadherin or annexin V. The reaction was started by addition of 1.5 mM $CaCl_2$ and allowed to proceed for 5 min. at 25° C. The reaction was stopped with EDTA and the quantity of factor Xa formed was determined as described above for the factor Xase assay.

Prothrombinase Assay

Cleavage of prothrombin to thrombin was measured in a two-step amidolytic substrate assay analogous to that for factor X activation as previously described (Reference 37). Factor Va, 1 nM; factor Xa, 6.2 pM; and lactadherin or annexin V at specified concentrations were incubated for 5 min. at 25° C. in a solution containing 150 mM NaCl, 50 mM Tris, 1.5 mM (for 4% PS, sonicated vesicles) or 5 mM (for the other PS content and/or vesicle size) $CaCl_2$, and 0.05% wt/vol ovalbumin, pH 7.8, prior to addition of 1 µM prothrombin. After 5 min at 25° C., the reaction was stopped by the addition of EDTA to a final concentration of 7 mM. Thrombin formation was assessed in a kinetic microplate reader immediately after addition of 0.1 mM chromogenic substrate S-2238. The results displayed in the figures are means of triplicates from a representative experiment.

Activated Partial Thromboplastin Time and Prothrombin Time Assays

Pooled normal plasma, anticoagulated with 1:9 dilution of 3.8% citrate, was stored at −80° C. until usage. All reagents were pre-warmed to 37° C. and assays were performed in triplicate. For the activated partial thromboplastin time (aPTT) assay 76 µl of plasma was mixed with 76 µl aPTT reagent (aPTT-SA, Helena Laboratories, Beaumont Tex.) and 76 µl of lactadherin diluted into tris-buffered saline. After 10 min. 76 µl of 25 mM $Ca^{++}$ was added to start the clotting reaction. Time to fibrin strand formation was measured with a fibrometer. The aPTT reagent was either used at full strength or diluted 1:16 in 100 µM ellagic acid, as indicated (to maintain a constant ellagic acid concentration as the phospholipid was diluted).

For the prothrombin time (PT) assay 100 µl plasma was mixed with 100 µl lactadherin in tris-buffered saline and 100 µl PT reagent (Thromboplastin-C Plus, Baxter, Miami, Fla.). Because package instructions call for use of the PT reagent at a 2:1 ratio with plasma, the PT reagent was supplemented to 16 mM $Ca^{++}$ to achieve the manufacturer's intended final $Ca^{++}$ concentration. The PT reagent was also diluted 1:24 in 16 mM $Ca^{++}$, then utilized in the same manner as full strength PT reagent.

Whole Blood Prothrombin Time Assay

Blood was drawn from healthy, nonsmoking, non-aspirin-using volunteers using 19-gauge butterfly needles. The first 3-ml of blood was discarded. Subsequently, 20 ml of blood was gently drawn. The blood was rapidly discharged into a polypropylene tube containing sodium citrate, final concentration 10 mM. To suppress contact activation, corn trypsin inhibitor was added to the tube (final concentration, 25 µg/ml). The blood was kept at room temperature, gently mixed by inversion approximately every 10 min. and was used within 3 hr of collection. For the clotting reaction 150 µl aliquots of blood were pre-warmed to 37° C. for 10 min then diluted 1:1 with 10 mM $CaCl_2$ and 50 pM relipidated tissue factor (0.38 µM phospholipid). The time to fibrin strand formation was monitored with a fibrometer. Experiments were performed in triplicate.

Results

We hypothesized that the tandem C domains of lactadherin confer phospholipid binding properties that enable it to compete with factor VIII and/or factor V for membrane binding sites and function as an anticoagulant. To test this hypothesis, we performed a competition membrane binding experiment in which lactadherin competed with fluorescein-labeled factor VIII for membrane binding sites (FIG. 1A).

For the experiments illustrated in FIG. 1A, fluorescein-labeled factor VIII, 4 nM, was mixed with the indicated concentration of competitor, lactadherin (σ) or annexin V (●) in the presence of 1.5 mM $Ca^{++}$. Liposheres were added and bound factor VIII was evaluated by flow cytometry after 10 min. Liposphere membrane composition was PS:PE:PC=4:20:76. The inhibition curve was modeled assuming that the $K_D$ of factor VIII with liposheres was 4.8 nM, the $K_i$ for lactadherin 0.5 nM (Reference 16).

The membranes had a composition of 4% PS, 20% PE, with the balance as PC. Bilayers were supported on 2 µm diameter glass microspheres (liposheres) and binding of factor VIII was evaluated by flow cytometry (Reference 16). Lactadherin effectively competed for all factor VIII binding sites with half-maximal displacement occurring at approximately 1.5 nM lactadherin. The competition predicted by a mathematical model approximated the data when lactadherin was assigned a $K_i$ of 0.5 nM.

For comparison with lactadherin, we determined if annexin V would compete for factor VIII binding sites in the same assay (FIG. 1A). Annexin V competed for approximately 20% of factor VIII binding sites at a concentration of 32 nM. These results indicate that lactadherin is a more potent competitor for the phospholipid binding sites of factor VIII on membranes with 4% PS.

To determine whether lactadherin is also able to recognize the phospholipid binding sites of factor V, we performed similar competition experiments with fluorescein-labeled factor V (FIG. 1B).

For the experiments illustrated in FIG. 1B, fluorescein-labeled factor V, 4 nM, was mixed with lactadherin (σ) or annexin V (●) and bound factor V was evaluated under the conditions described above. The inhibition curve was modeled assuming that the $K_D$ of factor V with liposheres was 4.3 nM, the $K_i$ for lactadherin, 1.0 nM (Reference 16).

Lactadherin competed efficiently for the binding sites recognized by factor V with half-maximal inhibition at an approximately 2-fold higher concentration. Annexin V competed for only 20% of the factor V binding sites at concentrations up to 32 nM. The corresponding $K_i$ for a curve approximating the data was 1.0 nM.

We performed factor Xase assays in the presence of increasing concentrations of lactadherin to determine whether the competition for factor VIII binding sites would translate into inhibition of the factor Xase complex (FIG. 1C).

For the experiments illustrated in FIG. 1C, lactadherin (σ) or annexin V (●) was mixed with factor IXa, 0.1 nM, and factor VI II, 1 nM, and factor X, 100 nM, prior to the addition of 1 µM sonicated vesicles with 1.5 mM $Ca^{++}$ and thrombin. The reaction was stopped after 5 min. and factor Xa was measured with chromogenic substrate S-2765 in a kinetic microplate reader. The phospholipid composition of the sonicated vesicles utilized was the same as for the binding experiments depicted in FIG. 1A. Lactadherin was an effective competitor for binding sites of factor VIII and factor V and potent inhibitor of the factor Xase complex with half-maximal inhibition at approximately 6 nM and >98% inhibition at 32 nM. Annexin V was an ineffective inhibitor of the factor Xase complex with less than 10% inhibition at 64 nM annexin V. These results confirm that lactadherin is able to inhibit the factor Xase complex, most likely by competing with factor VIIIa and/or factor IXa and factor X for phospholipid binding sites. They do not, however, explain why annexin V, which also binds to phospholipid membranes with high affinity, is an ineffective inhibitor under these conditions.

Figure 2:
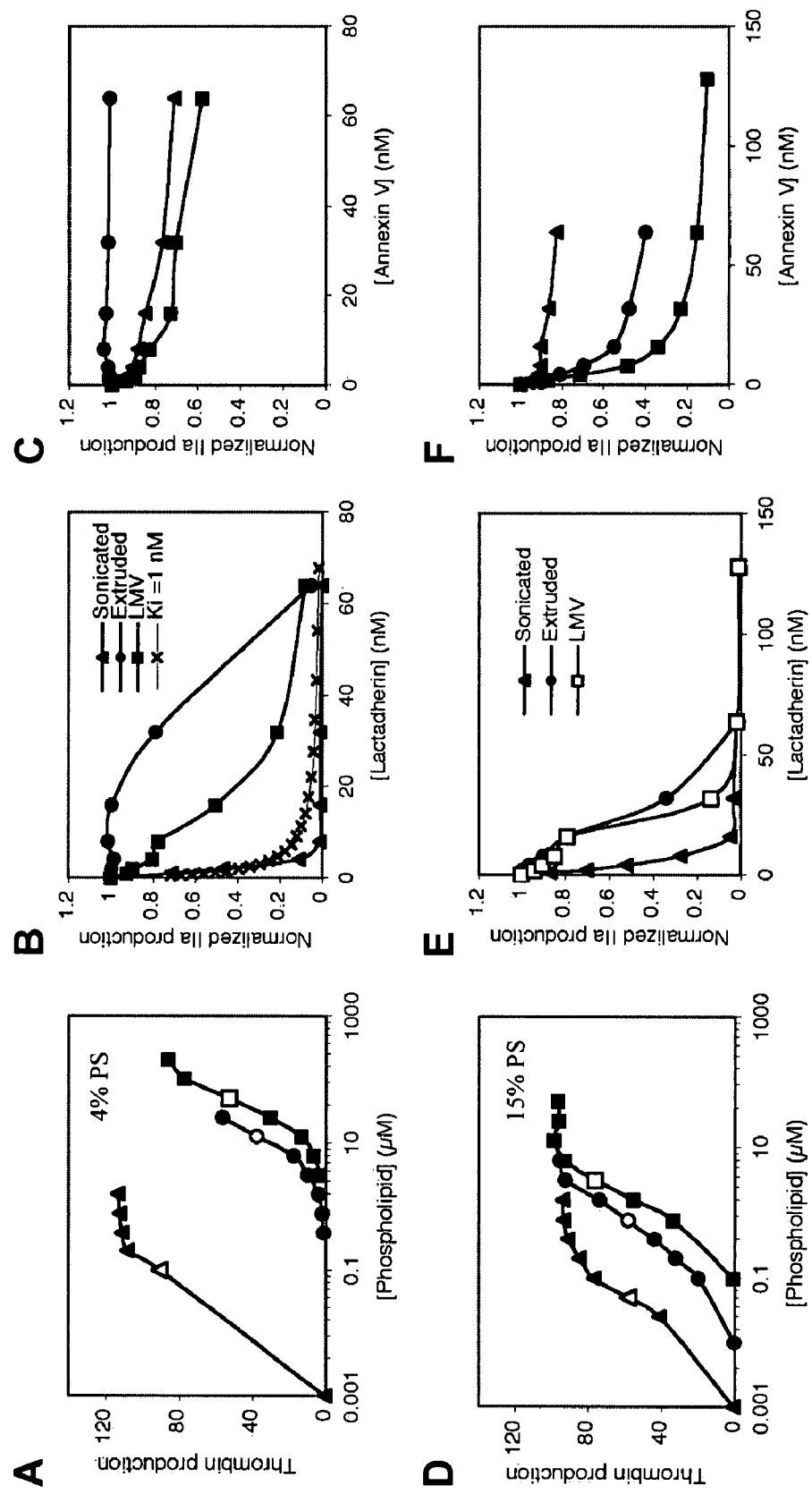
FIGS. 2A-F illustrate the relationship of vesicle curvature and PS content to inhibition of the prothrombinase complex by lactadherin or annexin V.

We determined whether lactadherin is capable of inhibiting the prothrombinase complex, in a manner similar to the factor Xase complex (FIGS. 2 A-F, where displayed results are from a single experiment representative of either two or three experiments for all conditions). Prior reports indicate that membrane binding and anticoagulant efficacy of annexin V is related to the PS content of membranes and inversely related to the curvature of phospholipid membranes (Reference 38). Thus, we evaluated vesicles with maximal curvature (sonicated-nominal diameter of 20 nm (Reference 39)) intermediate curvature (extruded-nominal diameter 73±25 nm (Reference 32)) and minimal curvature (large multilamellar vesicles-diameters >400 nm (Reference 30)) with both low PS content (4% PS—FIG. 2A-C) and high PS content (15% PS—FIGS. 2D-F).

For the experiments illustrated in FIGS. 2A-F, sonicated (σ and Δ), extruded (● and µ), and LMV (■ and □) contained 4% PS (FIGS. 2A-C) or 15% PS (FIGS. 2D-F). Effective concentrations of the vesicles for supporting the prothrombinase complex were identified in phospholipid titration experiments (FIGS. 2A and 2D). Subsaturating phospholipid concentrations were selected for inhibition experiments (open symbols in FIGS. 2A and 2D). The indicated phospholipid composition/concentration was added to factor Xa, factor Va, prothrombin, and either lactadherin or annexin V. After 5 min. the reaction was quenched with EDTA and thrombin measured with chromogenic substrate S-2238 in a kinetic microplate reader. Lactadherin was an effective inhibitor of the prothrombinase complex regardless of membrane curvature or PS content (FIGS. 2B and 2E). In contrast, inhibition by annexin V was inversely related to curvature and directly related to PS content (C, F). The $Ca^{++}$ concentration was 1.5 mM for sonicated vesicles of 4% PS (σ in A, B, C) and 5 mM for all other conditions.

The effectiveness of the vesicles for supporting prothrombinase complex decreased as the curvature decreased with sonicated vesicles of 4% PS producing 90% of the maximum thrombin production at a concentration of 0.1 µM phospholipid and much higher concentrations required for extruded vesicles and large multilamellar vesicles (LMV) (FIG. 2A). We compared effects of lactadherin and annexin V on thrombin formation utilizing the phospholipid concentrations (indicated by open symbols in FIG. 2A). We maintained the $Ca^{++}$ concentration at 1.5 mM, equivalent to plasma, for sonicated vesicles with 4% PS to test the reproducibility of results in FIGS. 1A-C. However, we increased the $Ca^{++}$ concentration to 5 mM for all other vesicles in order to optimize binding conditions for annexin V. Results showed that >90% inhibition of thrombin production was effected by lactadherin in sonicated, extruded and LMV. Our results confirmed that sonicated vesicles provide a substantially more potent surface for the prothrombinase complex than vesicles of larger diameter, particularly when the PS content is 4%. In contrast, annexin V was ineffective for sonicated vesicles and reached only 25-40% inhibition on extruded vesicles and LMV at 64 nM.

Lactadherin was an efficient inhibitor of the prothrombinase complex on all vesicles containing 15% PS (FIG. 2E). The half-maximal inhibitory concentrations of lactadherin varied with vesicle type. The limiting concentrations of phospholipids for experiments in FIG. 2B facilitated comparison of actual inhibition to that predicted by a $K_i$ of 1.0 nM, as depicted in FIG. 1B. (The term "$K_i$" is used to indicate only competition of lactadherin for binding sites of factor V(a) or factor VIII(a) when phospholipid binding sites are limiting.) The inhibition curve approximates the data obtained with sonicated vesicles. The variation in the concentration of lactadherin required for different vesicle types (FIGS. 2B and 2E) could be rationalized by assuming that lactadherin binds well to all types of phospholipid vesicles and that the higher phospholipid concentrations of extruded vesicles and LMV required more lactadherin to saturate the surface. In contrast to lactadherin, annexin V was only an effective inhibitor on LMV when the PS content was 15% (FIGS. 2C and 2F). Under these conditions Annexin V inhibited approximately 90% of prothrombinase activity at 128 nM concentration, similar to results in a prior report (References 38 and 40). Annexin V was not as effective as lactadherin under any conditions evaluated. These results indicate that lactadherin efficiently inhibits the prothrombinase complex and that, in contrast to Annexin V, inhibition is not closely tied to PS content or to vesicle curvature.

We determined whether inhibition of the factor Xase complex by annexin V and lactadherin may also be related to PS content of membranes and membrane curvature (FIGS. 3A-F, where data are from a single set of experiments representative of two or three experiments for all conditions).

For the experiments illustrated in FIGS. 3A-F, sonicated (σ and Δ), extruded (● and µ), and LMV (■ and □) contained 4% PS (FIGS. 3A-C) or 15% PS (FIGS. 3D-F). Effective concentrations of the vesicles for supporting the factor Xase complex were identified in phospholipid titration experiments (FIGS. 3A and 3D). Subsaturating phospholipid concentrations were selected for inhibition experiments (open symbols in FIGS. 3A and 3D). Lactadherin was an effective inhibitor of Xase activity regardless of membrane curvature or PS content (FIGS. 3B and 3E). In contrast, inhibition by annexin V was inversely related to curvature and directly related to PS content (FIGS. 3C and 3F). Experimental conditions were as those for experiments illustrated in FIGS. 1A-C. The $Ca^{++}$ concentration was 1.5 mM for sonicated vesicles of 4% PS (a in FIGS. 3A-C) and 5 mM for all other conditions.

Our results indicate that, like the prothrombinase complex, the factor Xase complex is supported at lower concentrations of sonicated vesicles than extruded vesicles or LMV (FIGS. 3A and 3D). Also, the inhibition of the Xase activity on sonicated vesicles was approximated by a model in which lactadherin is assigned a $K_i$ of 0.5 nM (FIG. 3B), similar to the value correlating to direct competition for factor VIII binding sites (FIG. 1A). Lactadherin inhibited factor Xase complex more than 95% on all vesicle types, similar to inhibition of the prothrombinase complex (FIGS. 3B and 3E). However, the difference between the lactadherin concentrations required for inhibition of the factor Xase complex on sonicated vs. extruded vesicles and LMV was not as large as for the prothrombinase complex (FIGS. 2B and 2E). Annexin V was a more effective inhibitor of the factor Xase complex than the prothrombinase complex with inhibition reaching 80% for LMV of 4% PS (FIG. 3C) and 95% for LMV of 15% PS (FIG. 3F). However, Annexin V remained a poor inhibitor of the factor Xase complex on sonicated vesicles, with <20% inhibition for 4% PS and <50% for 15% PS. Together these results indicate that lactadherin is a potent, near-complete inhibitor of the prothrombinase and factor Xase complexes on synthetic membranes regardless of membrane curvature and over a wide range of PS content.

FIGS. 4A-B illustrate inhibition of the factor VIIa-tissue factor complex by lactadherin or annexin V. Recombinant tissue factor was reconstituted into vesicles of composition PS:PE:PC, 4:20:76 by detergent dialysis with tissue factor:PL ratio of 1:7500. The indicated concentrations of phospholipid, with included tissue factor, were incubated with the indicated concentrations of lactadherin or annexin V, 100 pM factor VIIa, 100 nM factor X, and 1.5 mM $Ca^{++}$ for 5 min prior to addition of EDTA and the chromogenic substrate S-2765. Lactadherin inhibited function of the factor VIIa-tissue factor complex efficiently (FIG. 4A) while annexin V was less effective (FIG. 4B). Displayed data with tissue factor concentration of 1 nM (◇) are representative of three experiments. Data from experiments with a tissue factor concentration of 0.2 nM (μ) and 0.04 nM (σ) are representative of two experiments.

We determined whether Lactadherin might also have the capacity to inhibit the factor VIIa-tissue factor complex (FIG. 4A). Recombinant tissue factor was reconstituted into vesicles containing 4% PS, 20% PE by dialyzing octylthioglucoside away from the tissue factor-phospholipid mixture. Vesicles prepared in this way have curvature comparable to extruded vesicles (Reference 41). Lactadherin inhibited the factor VIIa-tissue factor complex more than 90%. The quantity of lactadherin required for 50% inhibition varied with the tissue factor concentration, and corresponding phospholipid concentration. Annexin V was a weaker inhibitor of the factor VIIa-tissue factor complex (FIG. 4B) with less than 50% inhibition at an annexin V concentration of 64 nM. These results indicate that lactadherin has the capacity to compete for membrane binding sites of blood coagulation proteins other than factor V and factor VIII.

Figure 5:
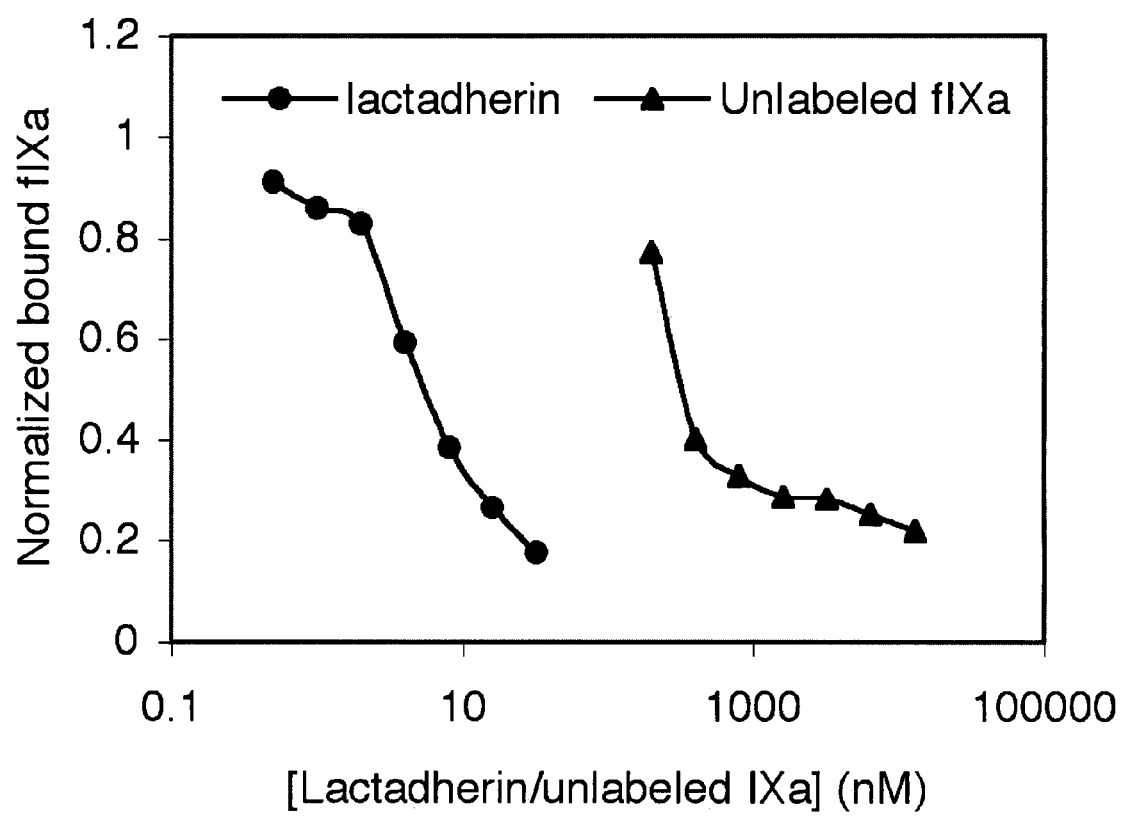
FIG. 5 illustrates competition for factor IXa binding sites by lactadherin.

To directly probe the possibility that lactadherin can compete with vitamin K-dependent blood coagulation proteins for membrane binding, we determined whether lactadherin is able to compete with fluorescein-labeled factor IXa (FIG. 5).

For the experiments illustrated in FIG. 5, the active site histidine of factor IXa was derivatized with fluorescein-Glu-Gly-Arg chloromethyl ketone as described under methods. Four nM fluorescein-labeled factor IXa was mixed with various concentrations of lactadherin or unlabeled factor IXa in the presence of 5 mM $Ca^{++}$ prior to the addition of lipospheres and evaluation of bound fluorescein-labeled factor IXa as described for FIGS. 1A-C. Lactadherin and unlabeled factor IXa both competed with labeled factor IXa for membrane binding sites. Results are displayed with the abscissa on a log scale to enable direct comparison. Displayed data are representative of two experiments.

Fluorescein-labeled factor IXa bound to lipospheres with a dissociation constant of approx. 0.5 μM (data not shown), consistent with prior reports of the membrane-binding affinity of factor IX/factor IXa. Unlabeled factor IXa competed with fluorescein-labeled factor IXa indicating that membrane binding was not enhanced by derivatization by fluorescein-Glu-Gly-Arg chloromethyl ketone at the active site. Lactadherin competed with fluorescein-labeled factor IXa for membrane binding sites to the same extent as unlabeled factor IXa. However, half-maximal inhibition occurred at approximately 4 nM lactadherin vs. 300 nM factor IXa.

In order to confirm that the mechanism through which lactadherin inhibits membrane-bound blood coagulation complexes is via competition for membrane binding sites, we performed experiments with varying phospholipid concentrations (FIGS. 6A-C).

For the experiments illustrated in FIGS. 6A-C, factor Xase complex (FIG. 6A) and prothrombinase complex (FIG. 6B) function on sonicated vesicles was evaluated at 0.1 (●), 0.5 (□), and 2.5 (σ) μM phospholipid concentrations in the presence of 1.5 mM $CaCl_2$. Function of the factor Xase complex in the absence of phospholipid was also evaluated (FIG. 6C). Inhibition by lactadherin at various concentrations was measured using two step amidolytic assays for the production of factor Xa (FIGS. 6A and 6C) or thrombin (FIG. 6B) as described above. The inhibitory concentration of lactadherin was directly related to phospholipid concentration. In the absence of phospholipid (FIG. 6C) lactadherin was an inefficient inhibitor of the factor Xase complex. Data obtained at various phospholipid concentrations were normalized for comparison of relative inhibition by lactadherin. Phospholipid composition was PS:PE:PC 4:20:76. Displayed data are from a single set of experiments (FIGS. 6A and 6B) or a single experiment representative of three experiments (FIG. 6C).

When the phospholipid vesicle concentration was limiting, lactadherin inhibited 50% activity of the factor Xase complex (FIG. 6A) and the prothrombinase complex (FIG. 6B) at a concentration of approx. 2 nM. The concentration required increased for each increment in the phospholipid concentration indicating that the required lactadherin is related to the phospholipid concentration rather than the concentrations of blood coagulation proteins. Furthermore, when the phospholipid concentration was 2.5 μM the factor Xase complex and prothrombinase complex maintained more than 90% activity at 8 nM lactadherin, a concentration that inhibits activity more than 90% when the phospholipid concentration is limiting.

As noted above, we also evaluated the effect of lactadherin on the factor VIIIa-factor IXa complex in the absence of phospholipid (FIG. 6C). The concentrations of factor VIIIa, factor IXa, and factor X were chosen to be at or below their apparent $K_D$'s or $K_M$, respectively, thus optimizing the sensitivity of the reaction to inhibitory action of lactadherin. Lactadherin caused less than 50% inhibition at concentrations up to 512 nM. Thus, lactadherin is at least 1,000-times better inhibitor in the presence of phospholipid membranes.

These results indicate that the only mechanism through which lactadherin inhibits the factor Xase and prothrombinase complexes at the concentrations employed is by competitive occupation of phospholipid binding sites and that protein-protein complexes between lactadherin and factor VIIIa, factor Va, factor IXa, or factor X do not occur, or do not significantly inhibit function of these enzyme complexes.

To further investigate the dependence of lactadherin's inhibitory properties on phospholipid concentration, we evaluated inhibition of plasma clotting in activated partial thromboplastin time (aPTT) and prothrombin time (PT) assays. Commercial aPTT and PT reagents contain high concentrations of phospholipids of unknown or unspecified composition. Lactadherin inhibited the aPTT assay by approx. 10% at a concentration of 1,000 nM and had no effect at 100 nM or lower concentrations. However, when the aPTT reagent was diluted to 6% of the original concentration the aPTT was prolonged 5%, 20%, and 1000% at concentrations of 10, 100, and 1,000 nM, respectively. Similarly, 1,000 nM lactadherin inhibited the prothrombin time by <20% when the PT reagent was present at 50% of manufacturer's suggested usage. However, when the PT reagent was diluted to 2% of the stock concentration the PT was prolonged 5%, 30%, and 500% by lactadherin concentrations of 10, 100, and 1,000 nM, respectively. These results are consistent with the model in which the major mechanism through which lactadherin inhibits blood coagulation enzyme complexes is through competition for phospholipid binding sites. Further studies, with defined phospholipid membranes are recommended to determine whether the apparent $K_i$'s for inhibition of the isolated prothrombinase and Xase complexes correlate to inhibitory concentrations for plasma.

The results above, showing inhibition of the factor Xase, the prothrombinase and the factor VIIa-tissue factor complexes support the hypothesis that lactadherin would inhibit the rate at which whole blood clots. To test this prediction, we utilized a modified whole blood prothrombin time (FIG. 7).

Figure 7:
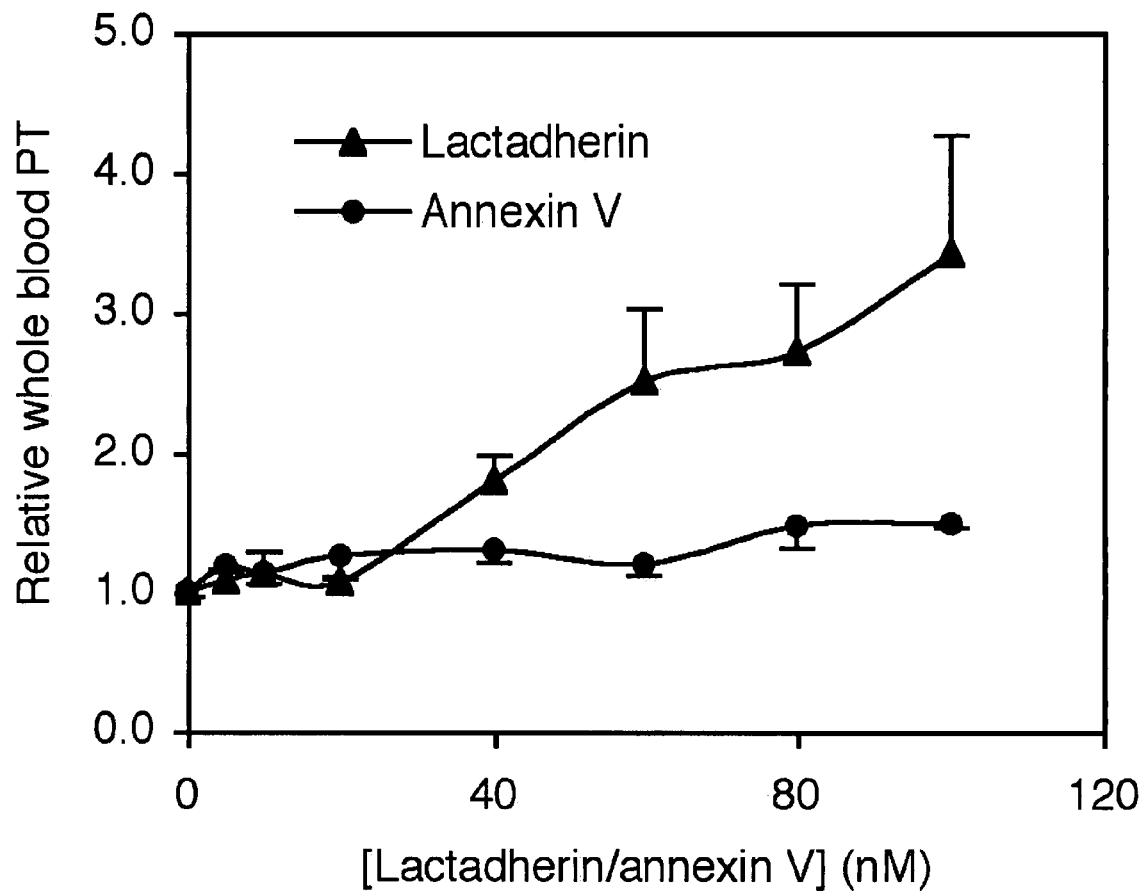
FIG. 7 illustrates inhibition of whole blood prothrombin time by lactadherin or annexin V.

For the experiments illustrated in FIG. 7, fresh whole blood was anticoagulated with 10 mM citrate and 25 µg/ml corn trypsin inhibitor (to minimize activation of the intrinsic pathway prior to the prothrombin time assay) in a polypropylene tube. After addition of indicated quantities of lactadherin (σ) or annexin V (●), the blood was diluted 1:1 with 50 pM tissue factor and 10 mM $Ca^{++}$. Time to fibrin strand formation was measured with a fibrometer. Blood coagulation was initiated by simultaneous addition of calcium and 50 pM tissue factor prepared as in FIGS. 4A-B. Results are displayed as the ratio of prothrombin time for blood treated with annexin V or lactadherin to prothrombin time for control blood from the same donor, with the same elapsed time since phlebotomy. Displayed results are mean±SD for triplicate samples from a single experiment representative of three experiments.

In the absence of lactadherin or annexin V, the time to clot varied between 1200 and 2000 seconds for different donors. Lactadherin and annexin V led to prolongation of the clotting time and the prolongation was similar over a concentration range of 0-20 nM. However, at concentrations of 40 nM and above lactadherin led to progressively longer inhibition of blood clotting. The clotting time was prolonged approximately 3-fold at 100 nM lactadherin, but only about 1.5-fold by annexin V. These results indicate that Lactadherin competes for binding sites on cell membranes to inhibit blood coagulation in a manner similar to inhibition of isolated blood coagulation complexes on phospholipid vesicles.

Our results indicate that lactadherin binds to PS-containing membranes with sufficient affinity to compete with blood coagulation proteins. The phospholipid-binding competition makes lactadherin a potent inhibitor of the prothrombinase, the factor Xase, and the factor VIIa-tissue factor complexes of blood coagulation. Because the quantity of lactadherin necessary to inhibit these enzyme complexes is proportional to the phospholipid concentration employed, and because lactadherin does not efficiently inhibit the phospholipid-free factor VIIIa-factor IXa complex, the major mechanism of inhibition involves blocking of the phospholipid surface rather than formation of inhibitory protein-protein complexes. Inhibition of whole blood prothrombin time indicates that lactadherin binds to platelet membranes to inhibit blood coagulation in a mechanism similar to inhibition of reconstituted enzyme complexes on phospholipid vesicles.

The enzyme complexes of blood coagulation assemble and function efficiently only on a membrane surface. PS-containing membranes serve to increase the apparent affinity of the respective cofactors, factor VIIIa and factor Va, for the enzymes, factor IXa and factor X, and of the cofactor-enzyme complexes for the substrates, factors X and prothrombin, respectively (Reference 42). The membranes also serve as allosteric activators of the enzyme-cofactor complex (Reference 29). PS-containing membranes also support anticoagulant activity that modulates the procoagulant activity. For example, protein C is activated by the thrombin-thrombomodulin complex on PS-containing membranes (Reference 43) and activated protein C inactivates factor Va and factor VIIIa on PS-containing membranes (Reference 44). The membranes of quiescent blood cells do not display the PS necessary to enable assembly and function of the procoagulant enzyme complexes (References 45-46). Rather, it is exposed only after cells are stimulated or undergo apoptosis (Reference 47). In the setting of a tissue injury, the procoagulant membranes are probably on the surface of platelets that have adhered to the damaged tissues (Reference 48). The absence of a PS-containing phospholipid membrane effectively prevents function of the complexes. Thus, blocking the PS-containing phospholipid binding sites on platelets appears to be a potential mechanism for preventing blood coagulation or altering the procoagulant/anticoagulant balance. Additional investigation is recommended to determine whether lactadherin has this physiologic function.

Several proteins have been identified that can influence blood coagulation via interaction with phospholipid membranes. The hypothesis that lactadherin might function in this manner was based on the homology between the discoidin-type domains of lactadherin and those of factors VIII and V, together with the previously defined membrane-binding properties of lactadherin (Reference 6). Annexin V, the most thoroughly studied of these proteins, binds to PS-containing membranes with high affinity (Reference 25). However, annexin V binds poorly to curved membranes (Reference 40) requires supraphysiologic $Ca^{++}$ concentrations for optimal binding, and inhibits less than 80% of procoagulant function on endothelial cell membranes unless the concentration exceeds 200 nM (Reference 49). Likewise, annexin V is an incomplete inhibitor of the factor Xase complex on platelet membranes (Reference 50). Our results, indicating inhibition of the prothrombinase complex exceeds 80% at 60 nM annexin V only when the curvature of the membrane is minimal and the PS content is 15%, are in agreement with these prior studies. $\beta_2$-glycoprotein I binds to PS-containing membranes and other negatively charged lipid-containing particles such as lipoproteins. Purified $\beta_2$-glycoprotein I partially inhibits prothrombinase activity on purified platelets or phospholipid vesicles (Reference 51). However, $\beta_2$-glycoprotein I may be a more efficient inhibitor of the anticoagulant reaction in which activated protein C cleaves factor V or factor Va on a phospholipid membrane (Reference 52). $\beta_2$-glycoprotein I bound to phospholipid is the primary antigen of lupus-type anticoagulants (Reference 53). When an antibody links two β2-glycoprotein I molecules the membrane-binding affinity is increased and $\beta_2$-glycoprotein becomes a more potent in vitro anticoagulant (Reference 54). Whether $\beta_2$-glycoprotein I has a physiologic function influencing procoagulant or anticoagulant membrane interactions remains unknown (Reference 55). The physiologic relationship of these proteins and lactadherin to blood coagulation is a likely field for further investigation.

Factor VIII binds to sites on phospholipid membranes with remarkable specificity. The specificity is best illustrated by the failure of other lipid binding proteins to compete with factor VIII for these sites (Reference 16). Even factor V, with structural homology and equivalent affinity for phospholipid membranes competes for only a fraction of the sites recognized by factor VIII. The capacity of lactadherin to compete for membrane binding sites of factor VIII, also to inhibit both the factor Xase complex and the prothrombinase complex indicates that lactadherin is more promiscuous than factor VIII with regard to phospholipid binding sites (Reference 16). Inhibition of the factor VIIa-tissue factor complex indicates that lactadherin has the capacity to compete for the vitamin K dependent proteins, factor VIIa and/or factor X. The contrast between lactadherin and annexin V with regard to competing for membrane sites of both high and low PS content and varying membrane curvature indicate that lactadherin is also more promiscuous in its membrane requirements than annexin V. To facilitate understanding of these properties we have initiated studies to characterize the membrane binding properties of lactadherin vs. those of factor VIII and factor V. The results indicate that lactadherin resembles factor VIII and factor V in specific binding to PS and curvature-dependent membrane binding. However, lactadherin differs in having a lower PS requirement and no apparent requirement for PE on membranes with low PS content.

Figure 6:
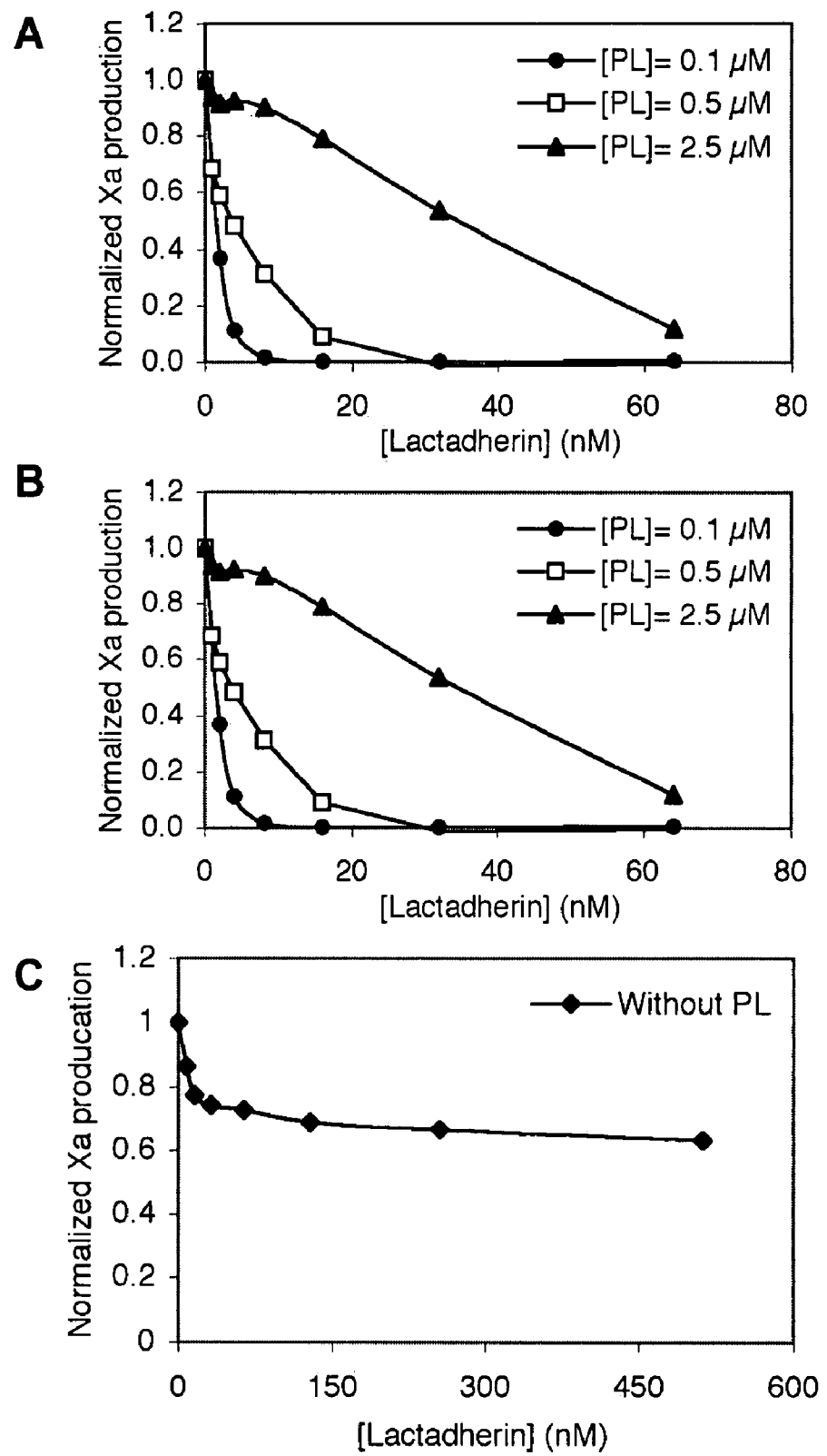
FIGS. 6A-C illustrate the relationship of inhibition by lactadherin to phospholipid concentration.

Comparing the displacement of factor VIII and factor V by lactadherin with the competition predicted from the simplest mathematical model (FIGS. 1A-C and 3A-F) supports two conclusions. First, lactadherin is a better competitor for factor VIII binding sites than for factor V binding sites with a $K_i$ that is two-fold lower. More potent competition for factor VIII binding sites correlated with a two-fold lower $K_i$ for the factor Xase complex vs. the prothrombinase complex not only under conditions where phospholipid was limiting but also when phospholipid was not limiting (FIG. 6). The lower $K_i$ value suggests that lactadherin binds with higher affinity to phospholipid binding sites of factor VIII vs. those of factor V. The second conclusion is that the experimental data did not precisely conform to the curves predicted by the mathematical model. The assumption of the model was that lactadherin competed for a single class of phospholipid binding sites with factor VIII or factor V. In other studies, we have further characterized the interaction of lactadherin with phospholipid binding sites. Our results indicate that lactadherin recognizes at least 2-classes of phospholipid binding sites so that both association and dissociation are kinetically complex events. The ability to interact with multiple classes of phospholipid binding sites explains part of the variation from the simple model as well as the mechanism underlying the capacity to compete with factor VIII and factor V with different apparent $K_u$'s.

Figure 3:
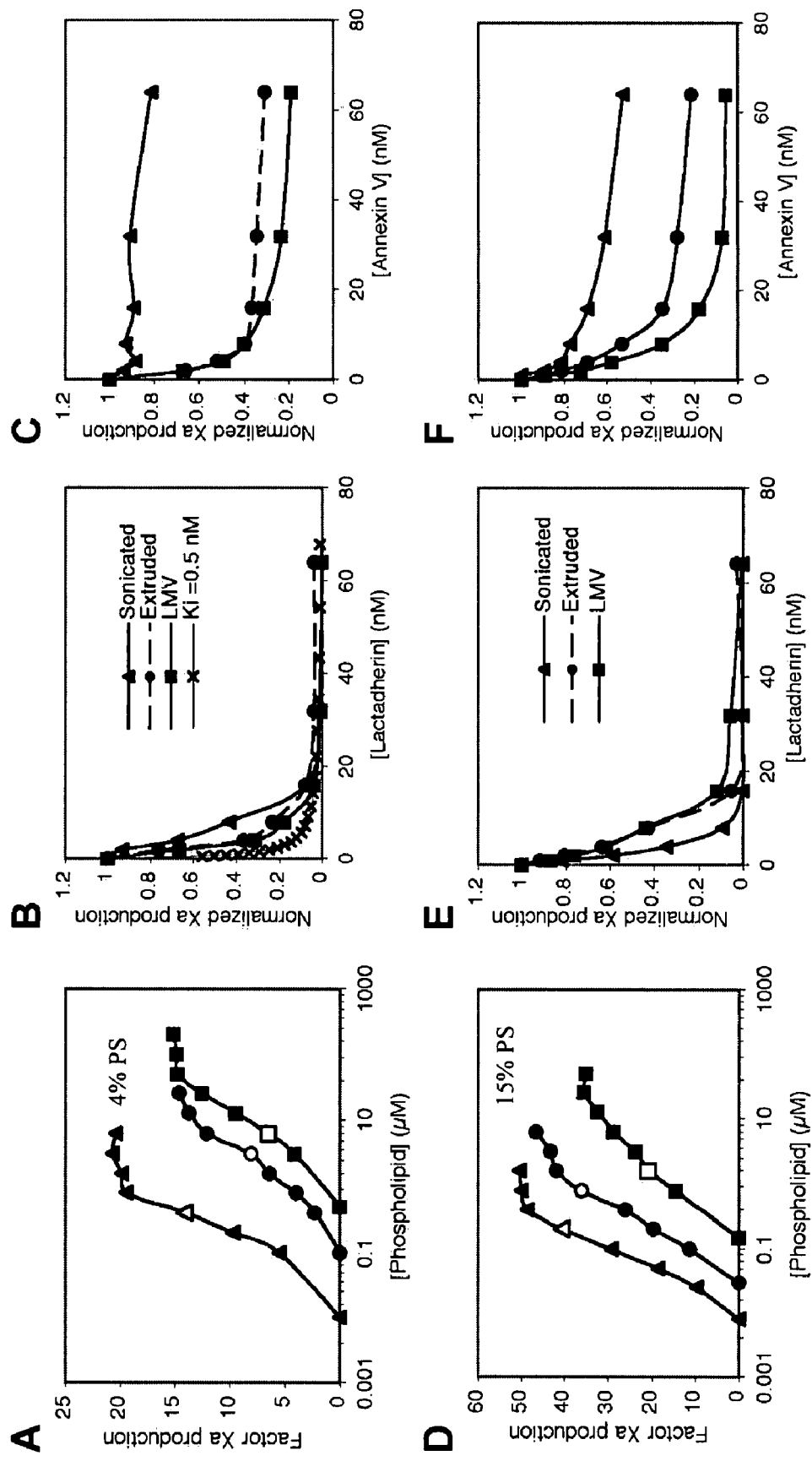
FIGS. 3A-F illustrate the relationship of vesicle curvature and PS content to inhibition of the factor Xase complex by lactadherin or annexin V.
Figure 4:
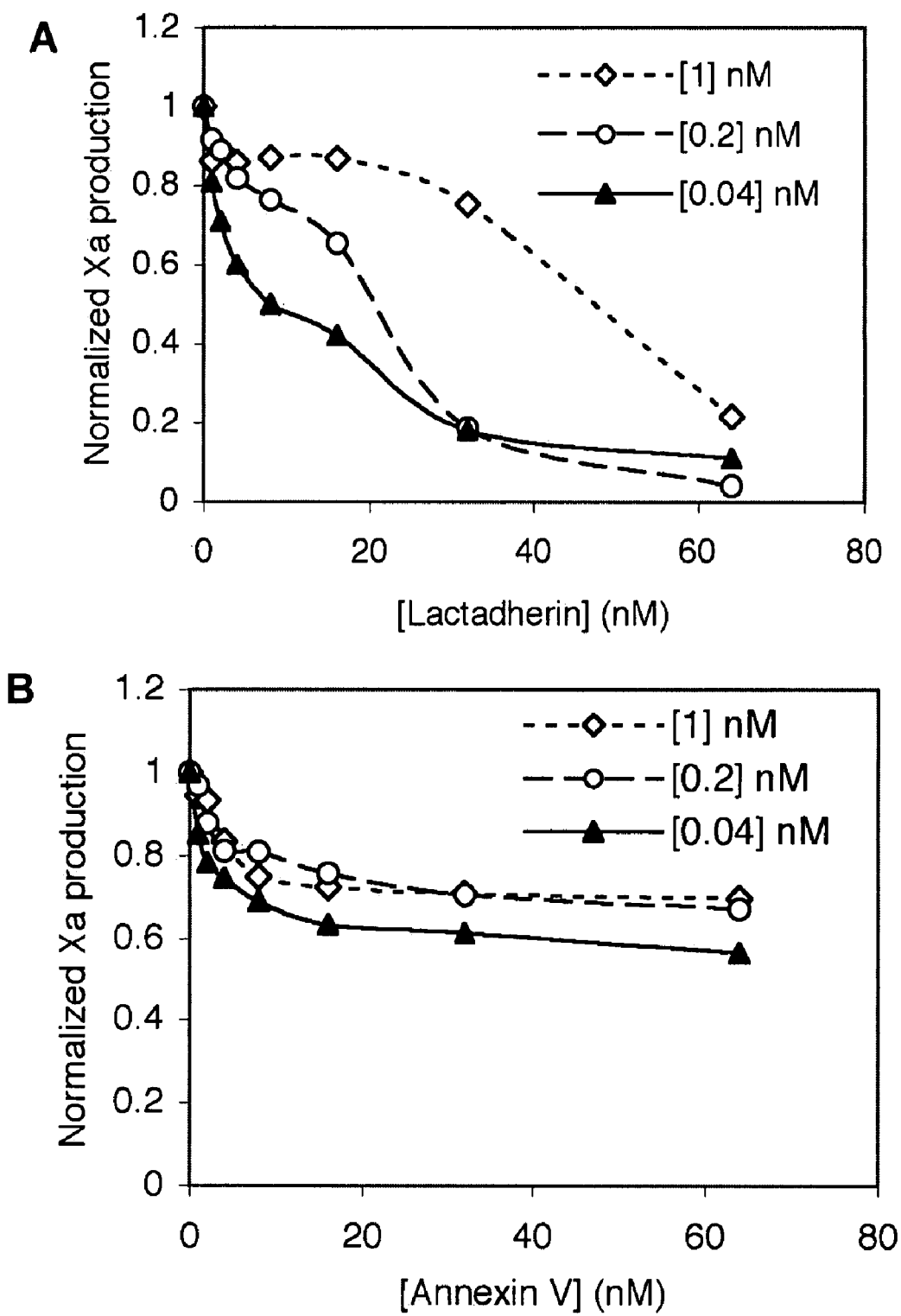
FIGS. 4A-B illustrate inhibition of the factor VIIa-tissue factor complex by lactadherin or annexin V.

The concentrations of lactadherin required to inhibit the whole blood prothrombin time were somewhat higher than the concentrations necessary to inhibit isolated enzyme complexes (compare FIGS. 2-4 vs. FIG. 6). Our data do not indicate whether these apparent discrepancies in concentration reflect lactadherin binding to a plasma protein that partially competes with binding sites on the membranes of platelets or other cells, or whether lactadherin may have a lower affinity for cell membranes vs. phospholipid vesicles.

The results of our experiments outlined above indicate that lactadherin could serve as a physiologic or pharmacologic anticoagulant. In newborn calves, the plasma concentration rises from 0.07 μg/ml before feeding to 1.2 μg/ml after feeding, suggesting that intact lactadherin is absorbed across the GI tract and that sufficient lactadherin circulates in the blood under these conditions to have a measurable in vitro anticoagulant effect (Reference 7). Lower concentrations of lactadherin have been measured in the serum of women with metastatic breast carcinoma but not in the serum of normal controls (Reference 56). The plasma levels in pregnant or lactating mammals have not been reported. However, it is plausible that sufficient lactadherin may be secreted into the blood or may "leak" from mammary glands to provide an anticoagulant effect during pregnancy or lactation. The relatively small size of lactadherin suggests that it freely traverses the placental barrier and could affect the procoagulant/anticoagulant balance of a developing fetus. The presence of lactadherin on the apical surfaces of secretory epithelia other than breast tissue suggests that lactadherin may circulate in blood even during the non-pregnant state. Thus, it is plausible that lactadherin could provide a physiologic anticoagulant function under a variety of circumstances. Our data support the conclusion that lactadherin is a candidate for development as a pharmacologic anticoagulant. Lactadherin functions at steps that are early in the coagulation pathway and is apparently more potent than annexin V, the only other tested agent that functions by a similar mechanism.

In view of the above, we believe that:
a. Lactadherin may be used as an anticoagulant in human beings. Because of its unique mechanism of action it may prove useful in specific clinical situations such as diffuse intravascular coagulation of obstetrics or septic shock. The natural method in which it is produced by mammary glands and secreted in milk suggests that it would prove much cheaper to produce than most protein drugs. Depending upon its efficacy, it might have a market as broad as all pregnant women with blood clots or patients with atherosclerosis who are experiencing unstable angina or a heart attack.
b. Lactadherin may be used as an anti-inflammatory agent in human beings, particularly in circumstances where blood coagulation is associated with inflammatory reactions including cell signaling mediated by coagulation enzymes and tissue factor. An example of a clinical situation where lactadherin may have anti-inflammatory properties is in sepsis.
c. Lactadherin may be used to measure procoagulant phospholipid that circulates in the blood of patients. Because lactadherin completely blocks access to procoagulant phospholipid, it may be applied to laboratory assays as a method to block access of blood coagulation proteins from all circulating procoagulant phospholipids and to determine the residual coagulation activity.

d. Lactadherin may be used as a laboratory reagent to remove circulating phospholipids from the plasma of patients in order to measure the coagulation potential of plasma in the presence of defined phospholipid. For example, lactadherin might be covalently linked to a matrix such as sepharose and procoagulant lipids removed by passage over the matrix. It might then be possible to provide a sensitive assay for lupus-type anticoagulants.

e. Measurement of blood lactadherin concentrations may be useful to guide anti-coagulant or anti-inflammatory therapy. For example, lactadherin may be a natural anticoagulant during pregnancy, lactation, or neonatal life. Measurement may predict risk of thrombosis or guide therapy in case of thrombosis.

A pharmaceutical composition including lactadherin or a fragment of lactadherin, or a functionally equivalent agent thereof, may be prepared, in a conventional manner. In particular, a pharmaceutical composition made in accordance with the present invention would include lactadherin or a fragment of lactadherin, or a functionally equivalent agent thereof, in an amount sufficient to provide therapeutic and/or prophylactic benefit, in combination with one or more pharmaceutically or physiologically acceptable carriers, diluents or excipients. Compositions of the present invention may be formulated for any appropriate manner for administration, including, for example, oral, nasal, intravenous or intramuscular administration. Appropriate dosages, duration and frequency of administration would be determined by known factors, such as the condition of the patient, the type and severity of the disease and the method of administration.

While this invention has been described as having preferred ranges, steps, materials, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

The following references, to the extent that they provide exemplary procedural or other details supplementary to those set forth herein, are specifically incorporated herein by reference.

REFERENCES

1. Hvarregaard J, Andersen M H, Berglund L, Rasmussen J T, Petersen T E. Characterization of glycoprotein PAS-6/7 from membranes of bovine milk fat globules. Eur J Biochem. 1996; 240:628-636.
2. Stubbs J, Lekutis C, Singer K, et al. cDNA cloning of a mouse mammary epithelial cell surface protein reveals the existence of epidermal growth factor-like domains linked to factor VIII-like sequences. Proc Natl Acad Sci, USA. 1990; 87:8417-8421.
3. Couto J R, Taylor M R, Godwin S G, Ceriani R L, Peterson J A. Cloning and sequence analysis of human breast epithelial antigen BA46 reveals an RGD cell adhesion sequence presented on an epidermal growth factor-like domain. DNA Cell Biol. 1996; 15:281-286.
4. Andersen M H, Berglund L, Rasmussen J T, Petersen T E. Bovine PAS-6/7 binds $a_v b_5$ integrin and anionic phospholipids through two domains. Biochem. 1997; 36:5441-5446.
5. Taylor M R, Couto J R, Scallan C D, Ceriani R L, Peterson J A. Lactadherin (formerly BA46), a membrane-associated glycoprotein expressed in human milk and breast carcinomas, promotes Arg-Gly-Asp (RGD)-dependent cell adhesion. DNA Cell Biol. 1997; 16:861-869.
6. Andersen M H, Graversen H, Fedosov S N, Petersen T E, Rasmussen J T. Functional analyses of two cellular binding domains of bovine lactadherin. Biochem. 2000; 39:6200-6206.
7. Butler J E, Pringnitz D J, Martens C L, Crouch N. Bovine-associated mucoprotein: I. Distribution among adult and fetal bovine tissues and body fluids. Differentiation. 1980; 17:3140.
8. Newburg D S, Peterson J A, Ruiz-Palacios G M, et al. Role of human-milk lactadherin in protection against symptomatic rotavirus infection. Lancet. 1998; 351:1160-1164.
9. Peterson J A, Couto J R, Taylor M R, Ceriani R L. Selection of tumor-specific epitopes on target antigens for radioimmunotherapy of breast cancer. Cancer Res. 1995; 55:5847s-5851s.
10. Haggqvist B, Naslund J, Sletten K, et al. Medin: an integral fragment of aortic smooth muscle cell-produced lactadherin forms the most common human amyloid. Proc Natl Acad Sci USA. 1999; 96:8669-8674.
11. Ensslin M, Calvete J J, Thole H H, et al. Identification by affinity chromatography of boar sperm membrane-associated proteins bound to immobilized porcine zona pellucida. Mapping of the phosphorylethanolamine-binding region of spermadhesin AWN. Biol Chem Hoppe Seyler. 1995; 376:733-738.
12. Arai M, Scandella D, Hoyer L. Molecular basis of factor VIII inhibition by human antibodies. Antibodies that bind to the factor VIII light chain prevent the interaction of factor VIII with phospholipid. J Clin Invest. 1989; 83:1978-1984.
13. Foster P A, Fulcher C A, Houghten R A, Zimmerman T S. Synthetic factor VIII peptides with amino acid sequences contained within the C2 domain of factor VIII inhibit factor VIII binding to phosphatidylserine. Blood. 1990; 75:1999-2004.
14. Ortel T, Devore-Carter D, Quinn-Allen M, Kane W. Deletion analysis of recombinant human factor V: Evidence for a phosphatidylserine binding site in the second C-type domain. J Biol Chem. 1992; 267:4189-4198.
15. Gilbert G E, Furie B C, Furie B. Binding of human factor VIII to phospholipid vesicles. J Biol. Chem 1990; 265: 815-822.
16. Gilbert G E, Drinkwater D, Barter S, Clouse S B. Specificity of phosphatidylserine-containing membrane binding sites for factor VIII: Studies with model membranes supported by glass microspheres (Lipospheres). J Biol Chem. 1992; 267:15861-15868.
17. Gilbert G E, Drinkwater D. Specific membrane binding of factor VIII is mediated by O-phospho-L-serine, a moiety of phosphatidylserine. Biochem. 1993; 32:9577-9585.
18. Comfurius P, Smeets E F, Willems G M, Bevers E M, Zwaal R F A. Assembly of the prothrombinase complex on lipid vesicles depends on the stereochemical configuration of the polar headgroup of phosphatidylserine. Biochem. 1994; 33:10319-10324.

19. Gilbert G E, Arena A A. Phosphatidylethanolamine induces high affinity binding sites for factor VIII on membranes containing phosphatidyl-L-serine. J Biol Chem. 1995; 270:18500-18505.
20. Gilbert G E, Arena A A. Unsaturated phospholipid acyl chains are required to constitute membrane binding sites for factor VII. Biochem. 1998; 37:13526-13535.
21. Pratt K P, Shen B W, Takeshima K, et al. Structure of the C2 domain of human factor VIII at 1.5 angstrom resolution. Nature. 1999; 402:439-442.
22. Macedo-Ribeiro S, Bode W, Huber R. et al. Crystal structures of the membrane-binding C2 domain of human coagulation factor V. Nature. 1999; 402:434-439.
23. Kim S W, Quinn-Allen M A, Camp J T, et al. Identification of functionally important amino acid residues within the C2-domain of human factor V using alanine-scanning mutagenesis. Biochem. 2000; 39:1951-1958.
24. Peterson J A, Patton S, Hamosh M. Glycoproteins of the human milk fat globule in the protection of the breast-fed infant against infections. Biol Neonate. 1998; 74:143-162.
25. Tait J F, Gibson D, Fujikawa K. Phospholipid binding properties of human placental anticoagulant protein-1, a member of the lipocortin family. J Biol Chem. 1989; 264:7944-7949.
26. Crompton M R, Moss S E, Crumpton M J. Diversity in the lipocortin/calpactin family. Cell. 1988; 55:1-3.
27. Swairjo M A, Concha N O, Kaetzel M A, Dedman J R, Seaton B A. Ca2+-bridging mechanism and phospholipid head group recognition in the membrane-binding protein annexin V. Nat Struct Biol. 1995; 2:968-974.
28. Tait J F, Sakata M S, McMullen B A, et al. Placental anticoagulant proteins: Isolation and comparative characterization of four members of the lipocortin family. Biochem. 1988; 27:6268-6276.
29. Gilbert G E, Arena A A. Activation of the factor VIIIa-factor IXa enzyme complex of blood coagulation by membranes containing phosphatidyl-L-serine. J Biol Chem. 1996; 271:11120-11125.
30. Bangham A D, Standish M M, Watkins J C. Diffusion of univalent ions across the lamellae of swollen phospholipids. J Mol. Biol. 1965; 13:238-252.
31. Johnson S M, Bangham A D, Hill M W, Korn E D. Single bilayer liposomes. Biochim Biophys Acta. 1971; 233: 820-826.
32. Hope M J, Bally M B, Webb G, Cullis P R. Production of large unilamellar vesicles by a rapid extrusion procedure. Characterization of size distribution, trapped volume and ability to maintain a membrane potential. Biochim Biophys Acta. 1985; 812:55-65.
33. Chen P, Toribara T, Warner H. Anal Chem. 1956; 28:1756-1758.
34. Neuenschwander P F, Morrissey J H. Deletion of the membrane anchoring region of tissue factor abolishes autoactivation of factor VII but not cofactor function. Analysis of a mutant with a selective deficiency in activity. J Biol Chem. 1992; 267:14477-14482.
35. Lollar P, Fass D N. Inhibition of activated porcine factor IX by dansyl-glutamyl-glycyl-arginyl-chloromethylketone. Arch Biochem Biophys. 1984; 233:438-446.
36. Gilbert G E, Sims P J, Wiedmer T, et al. Platelet-derived microparticles express high affinity receptors for factor VIII. J Biol Chem. 1991; 266:17261-17268.
37. Govers-Riemslag J W, Janssen M P, Zwaal R F, Rosing J. Prothrombin activation on dioleoylphosphatidylcholine membranes. Eur J Biochem. 1994; 220:131-138.
38. Andree H A, Stuart M C, Hermens W T, et al. Clustering of lipid-bound annexin V may explain its anticoagulant effect. J Biol Chem. 1992; 267:17907-17912.
39. Huang C, Mason J. Geometric packing constraints in egg phosphatidylcholine vesicles. Proc Natl Acad Sci, USA. 1978; 75:308-310.
40. Andree H, Reutelingsperger C, Hauptmann R. et al. Binding of vascular anticoagulant a (VACa) to planar phospholipid bilayers. J Biol Chem. 1990; 265:4923-4928.
41. Ueno M, Tanford C, Reynolds J A. Phospholipid vesicle formation using nonionic detergents with low monomer solubility. Kinetic factors determine vesicle size and permeability. Biochem. 1984; 23:3070-3076.
42. Mann K G, Nesheim M E, Church W R, Haley P, Krishnaswamy S. Surface-dependent reactions of the vitamin K-dependent enzyme complexes. Blood. 1990; 76:1-16.
43. Freyssinet J M, Gauchy J, Cazenave J P. The effect of phospholipids on the activation of protein C by the human thrombin-thrombomodulin complex. Biochem J. 1986; 238:151-157.
44. Suzuki K, Stenflo J, Dahlback B, Teodorsson B. Inactivation of human coagulation factor V by activated protein C. J Biol Chem. 1983; 258:1914-1920.
45. Connor J, Schroit A. Transbilayer movement of phosphatidylserine in erythrocytes: Inhibition of transport and preferential labeling of a 31000-dalton protein by sulfhydryl reactive reagents. Biochem. 1988; 27:848-851.
46. Connor J, Bucana C, Fidler I J, Schroit A J. Differentiation-dependent expression of phosphatidylserine in mammalian plasma membranes: Quantitative assessment of outer-leaflet lipid by prothrombinase complex formation. Proc Natl Acad Sci USA. 1989; 86:3184-3188.
47. Fadok V A, Voelker D R, Campbell P A, et al. Exposure of phosphatidylserine on the surface of apoptotic lymphocytes triggers specific recognition and removal by macrophages. J Immunol. 1992; 148:2207-2216.
48. Bevers E, Comfurius P, Zwaal R. Changes in membrane phospholipid distribution during platelet activation. Biochim Biophys Acta. 1983; 736:57-66.
49. van Heerde W L, Poort S, van't Veer C, Reutelingsperger C P, de Groot P G. Binding of recombinant annexin V to endothelial cells: effect of annexin V binding on endothelial-cell-mediated thrombin formation. Biochem J. 1994; 302 (Pt 1):305-312.
50. London F, Ahmad S S, Walsh P N. Annexin V inhibition of factor IXa-catalyzed factor X activation on human platelets and on negatively-charged phospholipid vesicles. Biochem. 1996; 35:16886-16897.
51. Nimpf J, Bevers E M, Bomans P H, et al. Prothrombinase activity of human platelets is inhibited by beta 2-glycoprotein-1. Biochim Biophys Acta. 1986; 884:142-149.
52. Mori T, Takeya H, Nishioka J, Gabazza E C, Suzuki K. beta 2-Glycoprotein I modulates the anticoagulant activity of activated protein C on the phospholipid surface. Thromb Haemost. 1996; 75:49-55.
53. McNeil H P, Simpson R J, Chesterman C N, Krilis S A. Anti-phospholipid antibodies are directed against a complex antigen that includes a lipid-binding inhibitor of coagulation: beta 2-glycoprotein I (apolipoprotein H). Proc Natl Acad Sci USA. 1990; 87:4120-4124.
54. Takeya H, Mori T, Gabazza E C, et al. Anti-beta2-glycoprotein I (beta2GPI) monoclonal antibodies with lupus anticoagulant-like activity enhance the beta2GPI binding to phospholipids. J Clin Invest. 1997; 99:2260-2268.
55. Bancsi L F, van der Linden I K, Bertina R M. Beta 2-glycoprotein I deficiency and the risk of thrombosis. Thromb Haemost. 1992; 67:649-653.
56. Ceriani R L, Sasaki M, Sussman H, Wara W M, Blank E W. Circulating human mammary epithelial antigens in breast cancer. Proc Natl Acad Sci USA. 1982; 79:5420-5424.
57. Enoch H G, Striffmatter P. Formation of properties of 1000-A-diameter, single-bilayer phospholipid vesicles. Proceeding of the National Academy of Sciences, USA 1979; 76:145-149.

What is claimed is:

1. A method of inhibiting or reducing access to a procoagulant membrane by a coagulation molecule, comprising:
   a) providing a procoagulant membrane comprising a binding site containing phosphatidyl-L-serine; and
   b) adding lactadherin to the membrane wherein the lactadherin will bind to the binding site and reduce access for interaction by a coagulation molecule.

2. The method of claim 1, wherein:
a cell comprises the procoagulant membrane, the cell comprises at least one member selected from the group consisting of a platelet, an apoptotic cell, a necrotic cell, a blood cell, and a vascular cell.

3. The method of claim 1, wherein:
the procoagulant membrane comprises a phospholipid or a lipoprotein.

4. The method of claim 3, wherein:
the coagulation molecule comprises a blood coagulation protein.

5. The method of claim 3, wherein:
the coagulation molecule comprises at least one protein selected from the group consisting of prothrombin, factor V, factor Va, factor VII, factor VIIa, factor VIII, factor VIIIa, factor IX, factor IXa, factor Xa and factor X.

6. The method of claim 2, wherein:
the blood cell comprises a lymphocyte, a monocyte, a neutrophil, or an erythrocyte that has been stimulated or stressed to expose phosphatidyl-L-serine.

* * * * *

UNITED STATES PATENT AND TRADEMARK OFFICE
CERTIFICATE OF CORRECTION

PATENT NO.        : 7,354,897 B2
APPLICATION NO.   : 10/516450
DATED             : April 8, 2008
INVENTOR(S)       : Gary E. Gilbert et al.

It is certified that error appears in the above-identified patent and that said Letters Patent is hereby corrected as shown below:

The names of the inventors on the title page should read as follows:

(75) Inventors: Gary E. Gilbert, Winchester, MA (US);
Jialan Shi, Newton, MA (US)

Signed and Sealed this

Third Day of February, 2009

JOHN DOLL
*Acting Director of the United States Patent and Trademark Office*